(12) United States Patent
   Zubok

(10) Patent No.: US 11,160,671 B2
(45) Date of Patent: Nov. 2, 2021

(54) INTERVERTEBRAL DISC IMPLANTS AND TOOLING

(71) Applicant: Howmedica Osteonics Corp., Mahwah, NJ (US)

(72) Inventor: Rafail Zubok, Midland Park, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 60 days.

(21) Appl. No.: 16/513,921

(22) Filed: Jul. 17, 2019

(65) Prior Publication Data

US 2019/0336308 A1  Nov. 7, 2019

Related U.S. Application Data

(63) Continuation of application No. 14/708,959, filed on May 11, 2015, now Pat. No. 10,398,572, which is a (Continued)

(51) Int. Cl.
   *A61F 2/44*  (2006.01)
   *A61F 2/46*  (2006.01)
   (Continued)

(52) U.S. Cl.
   CPC ........ *A61F 2/4611* (2013.01); *A61B 17/1604* (2013.01); *A61B 17/1611* (2013.01); (Continued)

(58) Field of Classification Search
   CPC .......... A61F 2/442–4425; A61F 2/4611; A61F 2002/443
   See application file for complete search history.

(56) References Cited

U.S. PATENT DOCUMENTS 5,314,477 A  5/1994  Marnay et al.
5,722,977 A  3/1998  Wilhelmy
(Continued)

FOREIGN PATENT DOCUMENTS

WO  01/19295     3/2001
WO  03077808 A2  9/2003
(Continued)

OTHER PUBLICATIONS

European Search Report for EP 12152540.6 dated Feb. 27, 2012.
International Search Report, PCT/US2007/020562 dated Jun. 2, 2008.

*Primary Examiner* — Eduardo C Robert
*Assistant Examiner* — Steven J Cotroneo
(74) *Attorney, Agent, or Firm* — Lerner, David, Littenberg, Krumholz & Mentlik, LLP

(57) ABSTRACT

A kit for preparing an intervertebral disc space for receiving an implant (100) includes a plurality of trials (152) having different sizes. Each trial (152) includes a body (154) insertible into an intervertebral disc space, the body (154) having a leading end (162), a trailing end (164), a top surface (156) and a bottom surface (160), the top surface of the body having a first groove (176) formed therein. Each implant also includes a flange (166) secured to the trailing end (164) of the body (154), the flange (166) having a first channel (180) aligned with the first groove (176), wherein each of the different sized trials has a different flange thickness. The flange thickness controls advancement of a cutting tool such as a chisel (192) into the first groove at the top surface of the trial body, which controls the depth of the cut into vertebral bone.

20 Claims, 15 Drawing Sheets

Related U.S. Application Data continuation of application No. 12/442,181, filed as application No. PCT/US2007/020562 on Sep. 21, 2007, now abandoned.

(60) Provisional application No. 60/846,196, filed on Sep. 21, 2006.

(51) Int. Cl.
*A61B 17/16* (2006.01)
*A61B 17/17* (2006.01)
*A61F 2/30* (2006.01)

(52) U.S. Cl.
CPC ...... *A61B 17/1671* (2013.01); *A61B 17/1735* (2013.01); *A61B 17/1757* (2013.01); *A61F 2/442* (2013.01); *A61F 2/4425* (2013.01); *A61F 2/4684* (2013.01); *A61F 2/30767* (2013.01); *A61F 2002/3071* (2013.01); *A61F 2002/3082* (2013.01); *A61F 2002/30301* (2013.01); *A61F 2002/30616* (2013.01); *A61F 2002/30841* (2013.01); *A61F 2002/30884* (2013.01); *A61F 2002/30892* (2013.01); *A61F 2002/30904* (2013.01); *A61F 2002/449* (2013.01); *A61F 2002/4435* (2013.01); *A61F 2002/4627* (2013.01); *A61F 2230/0095* (2013.01); *A61F 2250/0087* (2013.01); *A61F 2250/0089* (2013.01)

(56) References Cited

U.S. PATENT DOCUMENTS

| | | | |
|---|---|---|---|
| 6,042,582 A | 3/2000 | Ray | |
| 6,063,088 A * | 5/2000 | Winslow | A61B 17/1757 606/86 A |
| 6,113,637 A | 9/2000 | Gill et al. | |
| 6,425,920 B1 | 7/2002 | Hamada | |
| 6,607,559 B2 | 8/2003 | Ralph et al. | |
| 6,896,676 B2 | 5/2005 | Zubok et al. | |
| 6,908,484 B2 | 6/2005 | Zubok et al. | |
| 6,972,037 B2 | 12/2005 | Zubok et al. | |
| 6,972,038 B2 | 12/2005 | Zubok et al. | |
| 6,994,728 B2 | 2/2006 | Zubok et al. | |
| 6,994,729 B2 | 2/2006 | Zubok et al. | |
| 6,997,954 B2 | 2/2006 | Zubok et al. | |
| 6,997,955 B2 | 2/2006 | Zubok et al. | |
| 7,083,625 B2 | 8/2006 | Berry | |
| 7,300,441 B2 | 11/2007 | Haid et al. | |
| 7,766,918 B2 | 8/2010 | Allard et al. | |
| 7,850,697 B2 | 12/2010 | Ross et al. | |
| 8,465,546 B2 * | 6/2013 | Jodaitis | A61F 2/4611 623/17.16 |
| 8,663,229 B2 * | 3/2014 | Marnay | A61B 17/1671 606/86 R |
| 2003/0032962 A1 | 2/2003 | McGahan et al. | |
| 2003/0233145 A1 | 12/2003 | Landry et al. | |
| 2004/0024406 A1 * | 2/2004 | Ralph | A61B 17/025 606/90 |
| 2004/0148027 A1 * | 7/2004 | Errico | A61F 2/4684 623/17.11 |
| 2004/0176772 A1 | 9/2004 | Zubok et al. | |
| 2004/0176773 A1 | 9/2004 | Zubok et al. | |
| 2004/0176774 A1 | 9/2004 | Zubok et al. | |
| 2004/0176777 A1 | 9/2004 | Zubok et al. | |
| 2004/0176778 A1 | 9/2004 | Zubok et al. | |
| 2004/0176843 A1 | 9/2004 | Zubok et al. | |
| 2004/0176851 A1 | 9/2004 | Zubok et al. | |
| 2004/0176852 A1 | 9/2004 | Zubok et al. | |
| 2004/0176853 A1 | 9/2004 | Sennett et al. | |
| 2004/0193272 A1 * | 9/2004 | Zubok | A61F 2/4425 623/17.11 |
| 2004/0215198 A1 | 10/2004 | Marnay et al. | |
| 2004/0220590 A1 | 11/2004 | Zubok et al. | |
| 2004/0220670 A1 | 11/2004 | Eisermann et al. | |
| 2004/0225295 A1 * | 11/2004 | Zubok | A61F 2/4425 606/90 |
| 2004/0243240 A1 | 12/2004 | Beaurain et al. | |
| 2005/0033305 A1 * | 2/2005 | Schultz | A61F 2/4611 606/99 |
| 2005/0055029 A1 | 3/2005 | Marik et al. | |
| 2005/0071013 A1 | 3/2005 | Zubok et al. | |
| 2005/0113842 A1 | 5/2005 | Bertagnoli et al. | |
| 2005/0240270 A1 | 10/2005 | Zubok et al. | |
| 2005/0240271 A1 | 10/2005 | Zubok et al. | |
| 2005/0240272 A1 | 10/2005 | Zubok et al. | |
| 2005/0273111 A1 | 12/2005 | Ferree et al. | |
| 2006/0030860 A1 * | 2/2006 | Peterman | A61F 2/4611 606/99 |
| 2006/0085011 A1 * | 4/2006 | Filippi | A61B 17/1757 606/99 |
| 2006/0241761 A1 | 10/2006 | Gately | |
| 2007/0123985 A1 * | 5/2007 | Errico | A61B 90/94 623/17.11 |
| 2007/0162130 A1 * | 7/2007 | Rashbaum | A61F 2/4611 623/17.11 |
| 2007/0270862 A1 | 11/2007 | Yu et al. | |
| 2007/0299276 A1 | 12/2007 | Feiring | |
| 2008/0045968 A1 | 2/2008 | Yu et al. | |
| 2009/0216330 A1 * | 8/2009 | Geisert | A61B 17/1671 623/17.16 |
| 2010/0298941 A1 | 11/2010 | Hes et al. | |

FOREIGN PATENT DOCUMENTS

| | | |
|---|---|---|
| WO | 2004041131 A2 | 5/2004 |
| WO | 2006033067 A2 | 3/2006 |
| WO | 2006130460 A2 | 12/2006 |

* cited by examiner

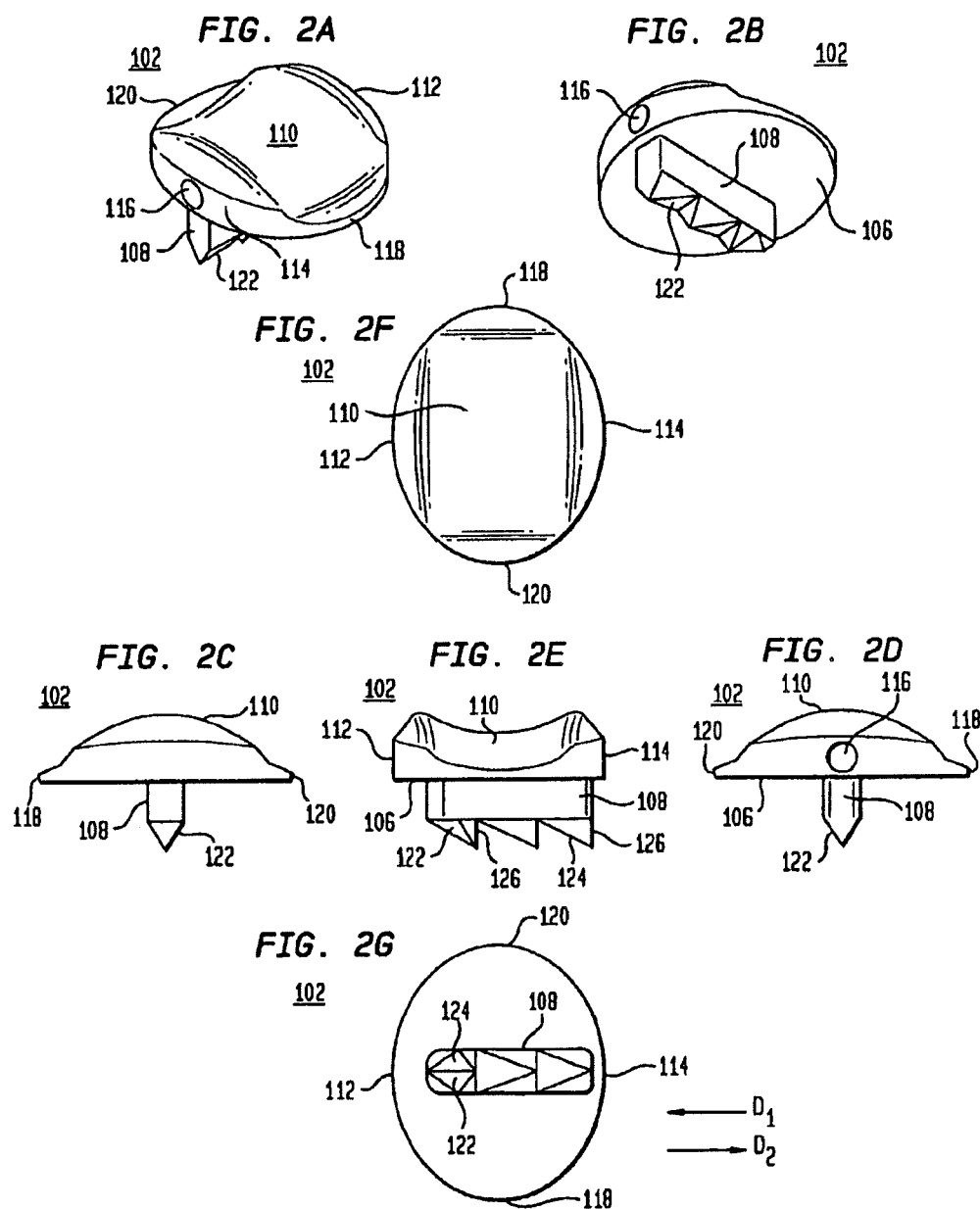

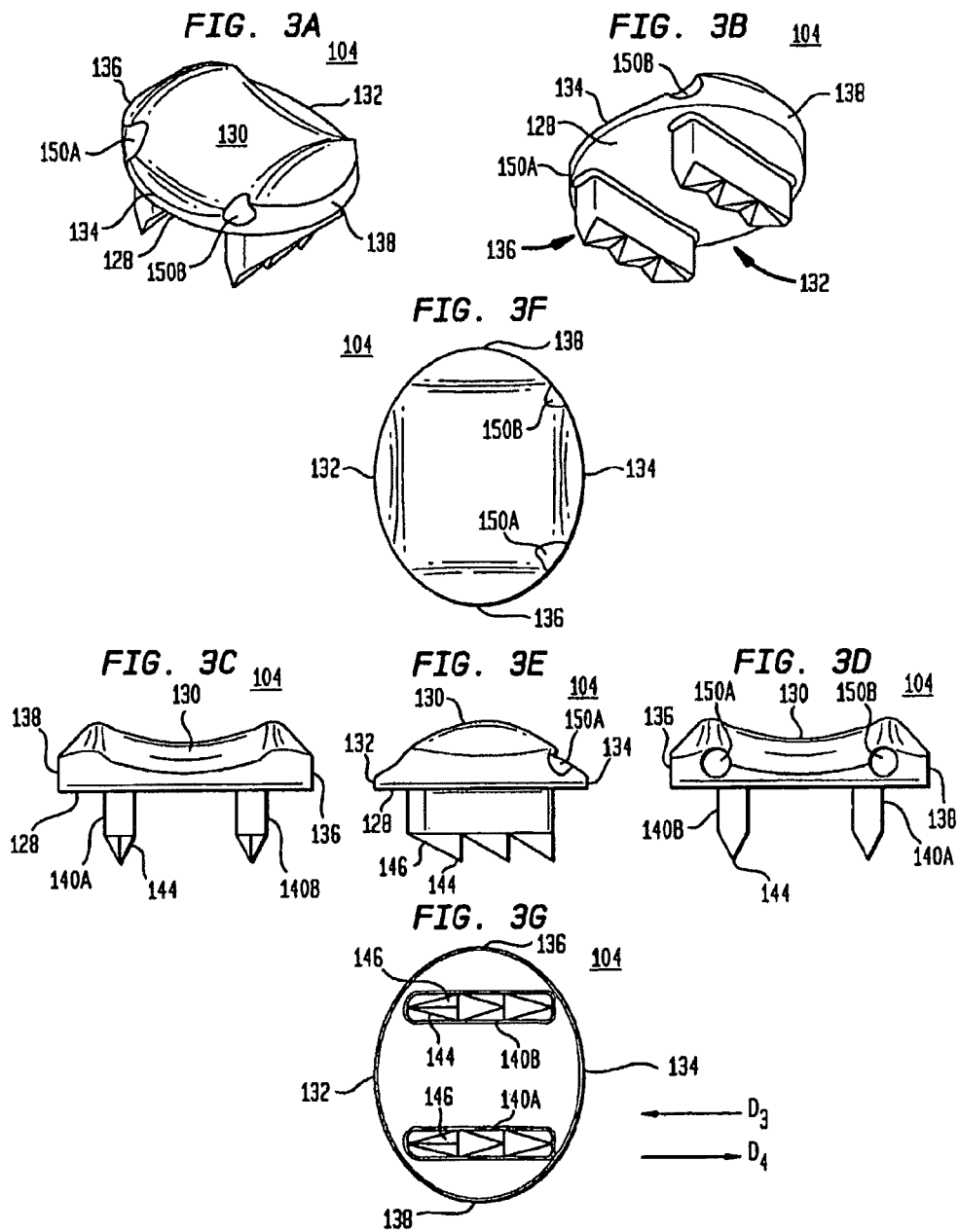

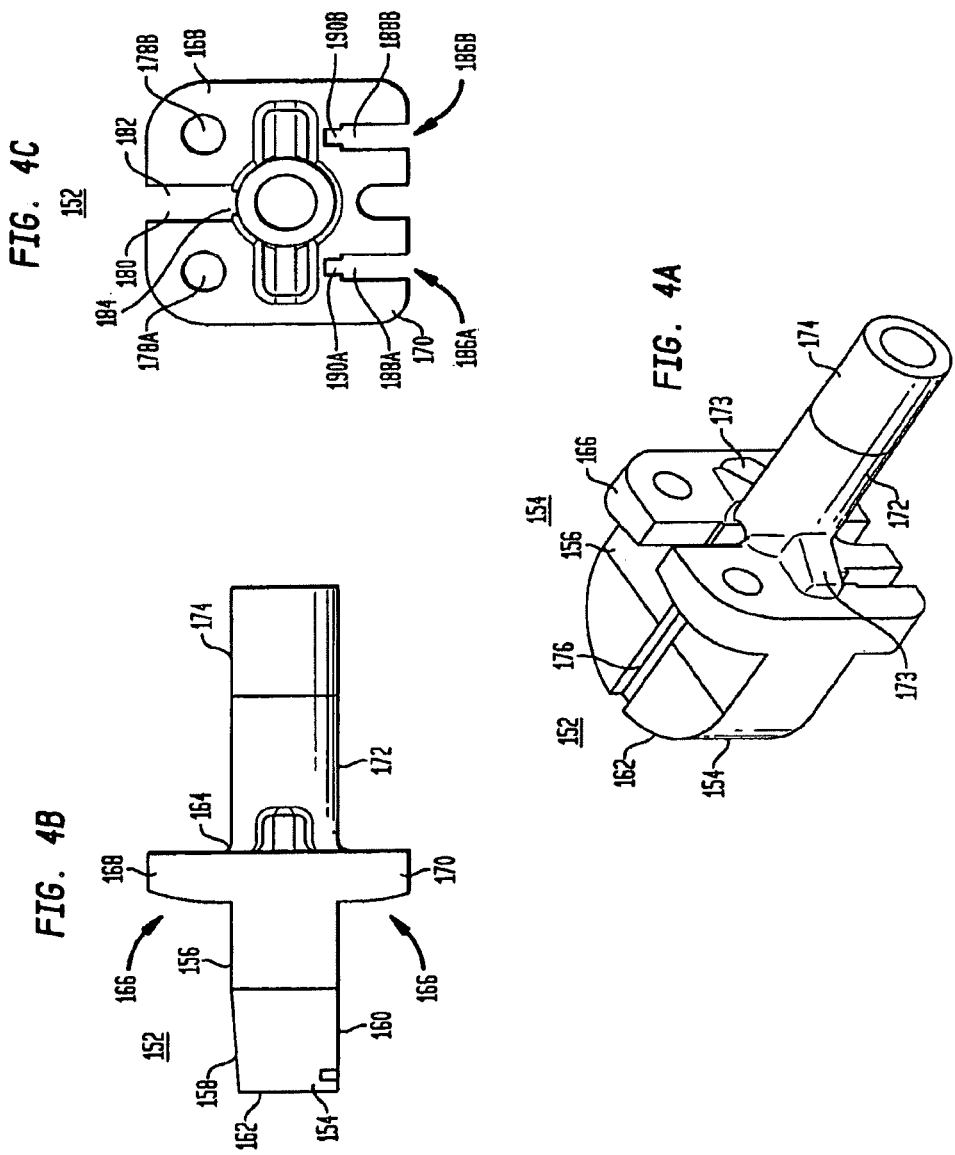

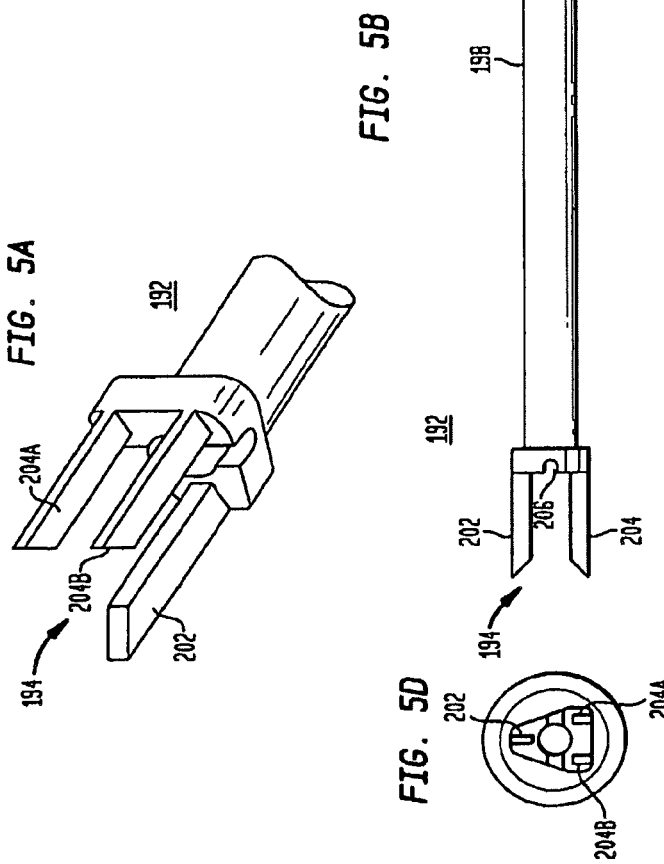

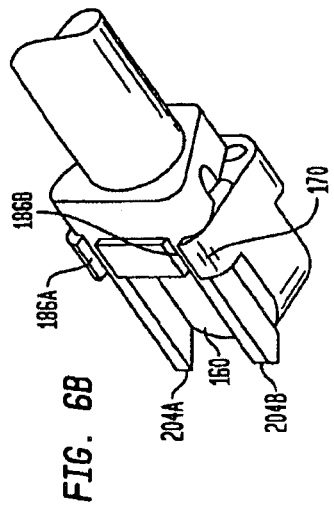
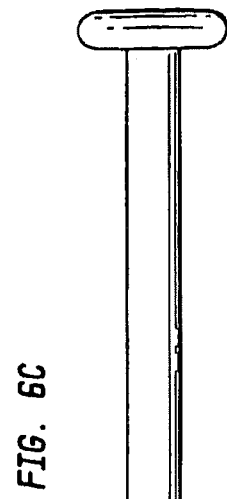
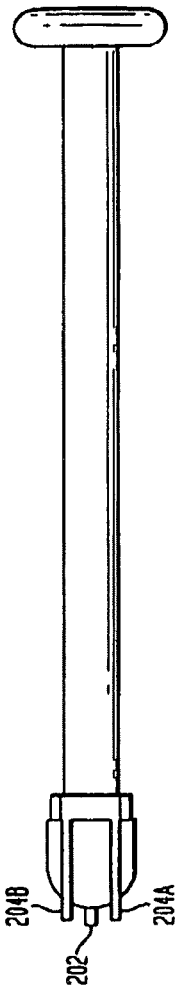
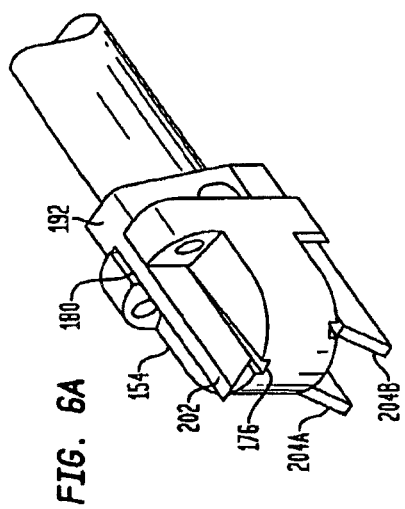
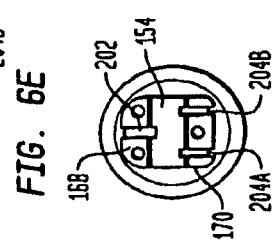
FIG. 6A
FIG. 6B
FIG. 6C
FIG. 6D
FIG. 6E

210

210

210

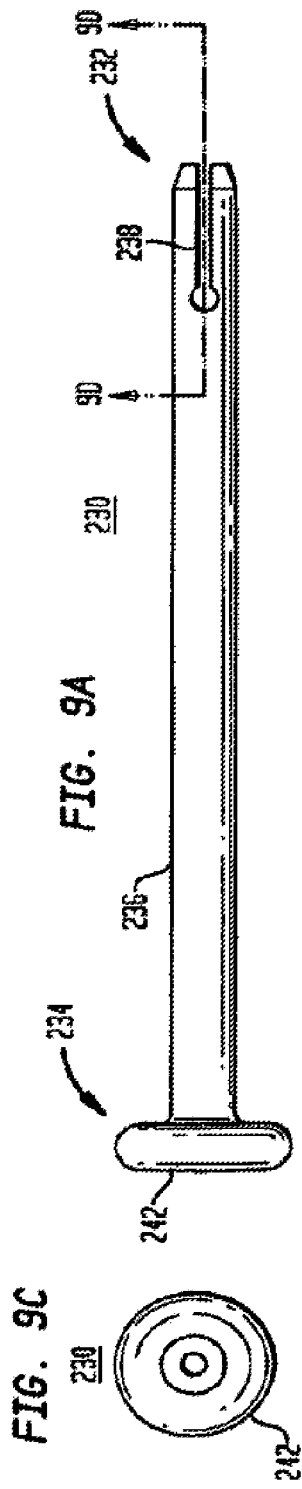
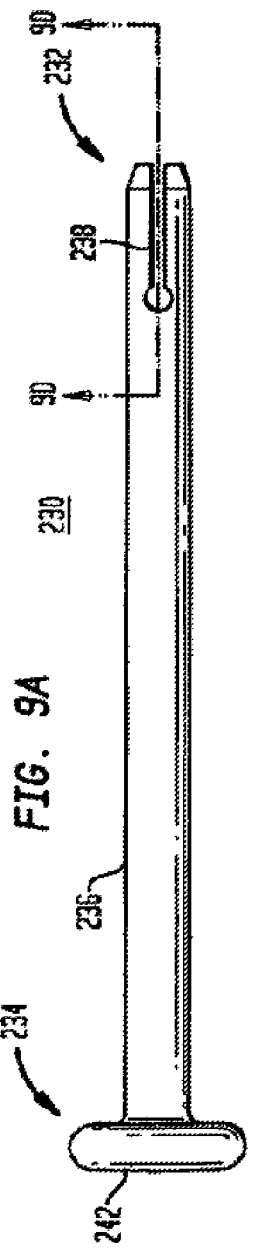
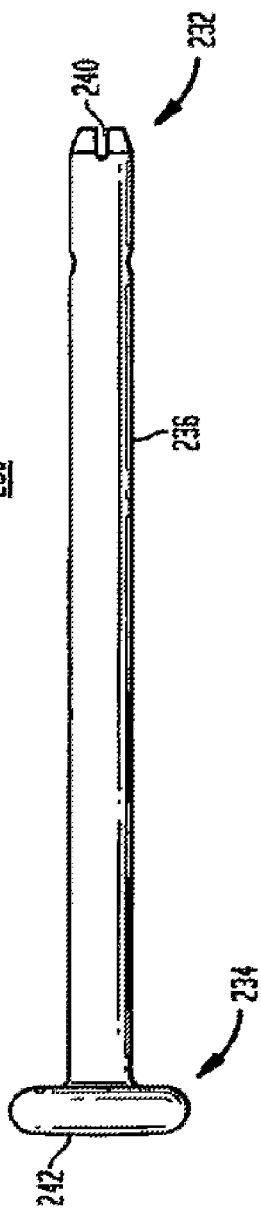
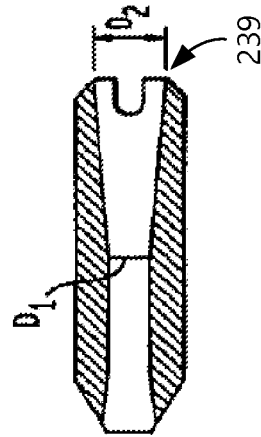
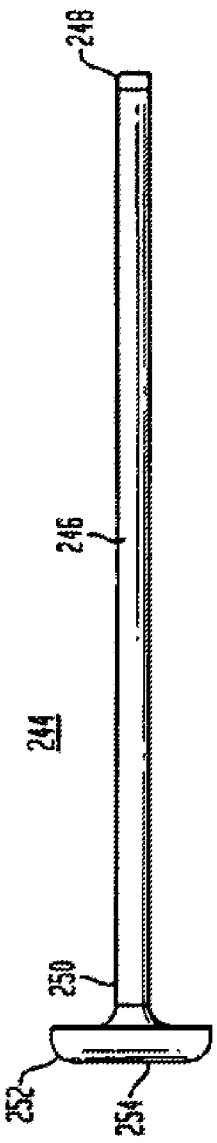
FIG. 9A
FIG. 9B
FIG. 9C
FIG. 9D
FIG. 10

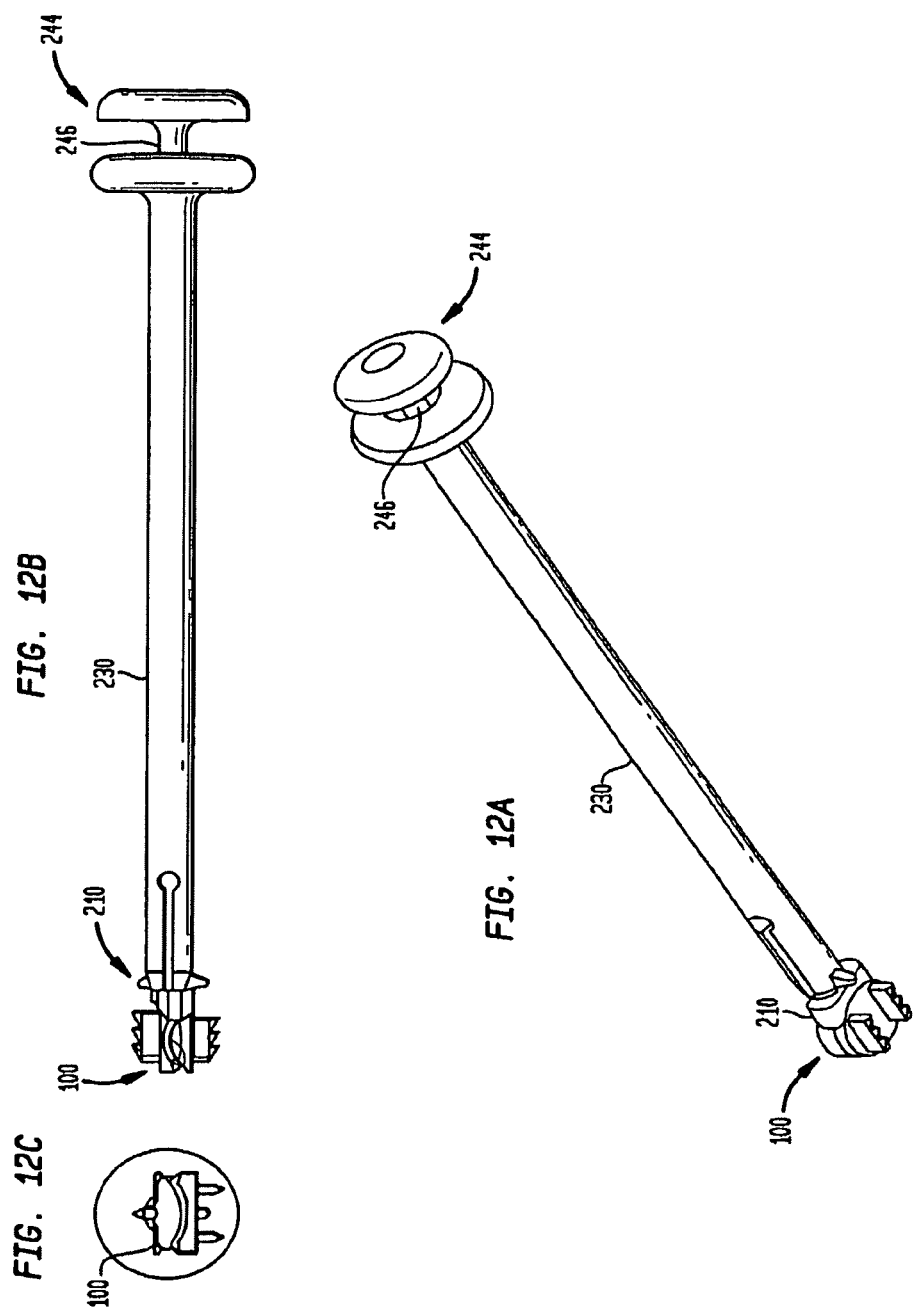

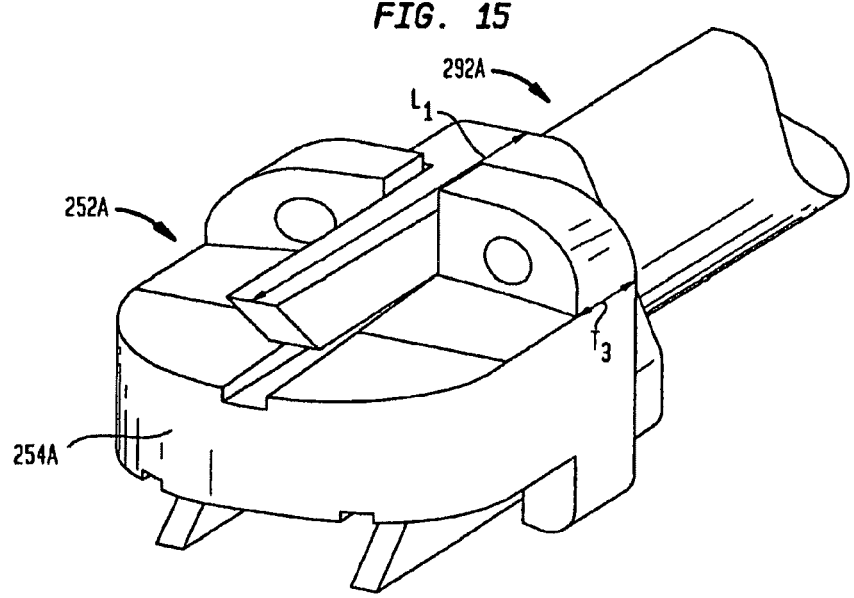
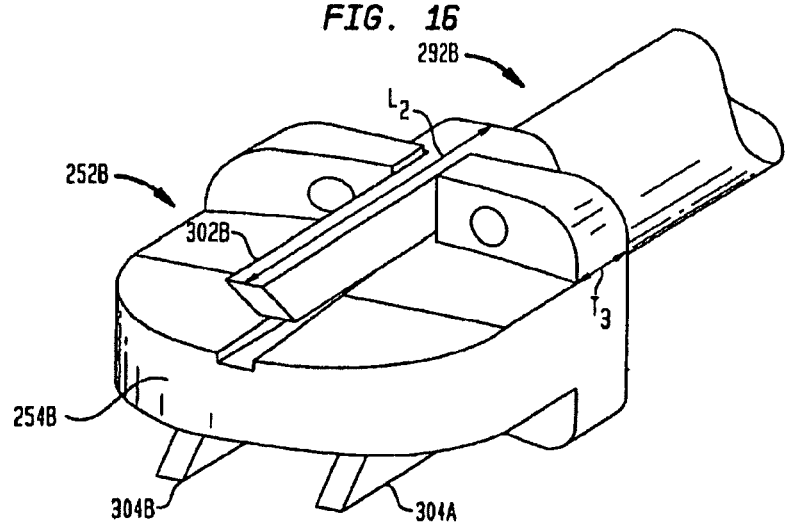

INTERVERTEBRAL DISC IMPLANTS AND TOOLING

CROSS-REFERENCE TO RELATED APPLICATIONS

The present application is a continuation of U.S. patent application Ser. No. 14/708,959, filed May 11, 2015, which is a continuation of U.S. patent application Ser. No. 12/442,181, filed Aug. 5, 2010, which is a national phase entry under 35 U.S.C. § 371 of International Application No. PCT/US2007/020562, filed Sep. 21, 2007, published in English, which claims benefit of U.S. Provisional Patent Application No. 60/846,196 filed Sep. 21, 2006. The disclosures of all of said applications are incorporated by reference herein.

The present application is related to U.S. patent application Ser. No. 11/439,808, filed May 24, 2006, which claims the benefit of U.S. Provisional Patent Application No. 60/790,415, filed Apr. 7, 2006, which claims the benefit of U.S. Provisional Patent Application No. 60/721,053, filed Sep. 27, 2005, which claims the benefit of U.S. Provisional Patent Application No. 60/701,306, filed Jul. 21, 2005, which claims the benefit of U.S. Provisional Patent Application No. 60/685,295, filed May 27, 2005, the disclosures of which are hereby incorporated by reference herein.

The present application also relates to U.S. Pat. No. 6,908,484, entitled "Cervical Disc Replacement" and filed on Mar. 6, 2003; U.S. Pat. No. 6,994,728, entitled "Cervical Disc Replacement Method" and filed on Feb. 11, 2004; United States Patent Application Publication No. 2004/0176851, entitled "Cervical Disc Replacement" and filed on Feb. 11, 2004; U.S. Pat. No. 6,994,729, entitled "Cervical Disc Replacement" and filed on Feb. 11, 2004; U.S. Pat. No. 6,997,955, entitled "Cervical Disc Replacement" and filed on Feb. 11, 2004; U.S. Pat. No. 6,972,037, entitled "Cervical Disc Replacement" and filed on Feb. 11, 2004; U.S. Pat. No. 6,972,038, entitled "Cervical Disc Replacement" and filed on Feb. 11, 2004; U.S. Pat. No. 6,997,954, entitled "Cervical Disc Replacement Method" and filed on Feb. 11, 2004; United States Patent Application Publication No. 2005/0240272, entitled "Cervical Disc Replacement" and filed on May 9, 2005; United States Patent Application Publication No. 2005/0240271, entitled "Cervical Disc Replacement" and filed on May 9, 2005; United States Patent Application Publication No. 2005/0240270, entitled "Cervical Disc Replacement" and filed on May 9, 2005; U.S. Pat. No. 6,896,676, entitled "Instrumentation And Methods For Use In Implanting A Cervical Disc Replacement Device" and filed on Oct. 17, 2003; United States Patent Application Publication No. 2004/0176773, entitled "Instrumentation And Methods For Use In Implanting A Cervical Disc Replacement Device" and filed on Feb. 18, 2004; United States Patent Application Publication No. 2004/0176843, entitled "Instrumentation And Methods For Use In Implanting A Cervical Disc Replacement Device" and filed on Feb. 18, 2004; United States Patent Application Publication No. 2004/0176778, entitled "Instrumentation And Methods For Use In Implanting A Cervical Disc Replacement Device" and filed on Feb. 18, 2004; United States Patent Application Publication No. 2004/0176777, entitled "Instrumentation And Methods For Use In Implanting A Cervical Disc Replacement Device" and filed on Feb. 18, 2004; United States Patent Application Publication No. 2004/0176852, entitled "Instrumentation And Methods For Use In Implanting A Cervical Disc Replacement Device" and filed on Feb. 18, 2004; United States Patent Application Publication No. 2004/0176774, entitled "Instrumentation And Methods For Use In Implanting A Cervical Disc Replacement Device" and filed on Feb. 18, 2004; United States Patent Application Publication No. 2004/0176772, entitled "Instrumentation And Methods For Use In Implanting A Cervical Disc Replacement Device" and filed on Feb. 18, 2004; United States Patent Application Publication No. 2004/0220590, entitled "Instrumentation And Methods For Use In Implanting A Cervical Disc Replacement Device" and filed on Feb. 18, 2004; United States Patent Application Publication No. 2005/0071013, entitled "Instrumentation And Methods For Use In Implanting A Cervical Disc Replacement Device" and filed on Nov. 19, 2004; and United States Patent Application Publication No. 2004/0193272, entitled "Instrumentation And Methods For Use In Implanting A Cervical Disc Replacement Device" and filed on Feb. 19, 2004, the disclosures of which are hereby incorporated by reference herein.

The present application also relates to U.S. Pat. No. 6,607,559, entitled "Trial Intervertebral Distraction Spacers" and filed on Jul. 16, 2001; U.S. patent application Ser. No. 10/436,039, entitled "Trial Intervertebral Spacers" and filed May 12, 2003; U.S. patent Ser. No. 10/128,619, entitled "Intervertebral Spacer Having A Flexible Wire Mesh Vertebral Body Contact Element" and filed Apr. 23, 2002; U.S. patent application Ser. No. 11/073,987, entitled Intervertebral Spacer Having A Flexible Wire Mesh Vertebral Body Contact Element; U.S. patent application Ser. No. 10/140,153, entitled "Artificial Intervertebral Disc Having A Flexible Wire Mesh Vertebral Body Contact Element" and filed May 7, 2002; U.S. patent application Ser. No. 10/151,280, entitled "Tension Bearing Artificial Disc Providing A Centroid Of Motion Centrally Located Within An Intervertebral Space" and filed May 20, 2002; U.S. patent application Ser. No. 10/175,417, entitled "Artificial Intervertebral Disc Utilizing A Ball Joint Coupling" and filed Jun. 19, 2002; U.S. patent application Ser. No. 10/256,160, entitled "Artificial Intervertebral Disc" and filed Sep. 26, 2002; U.S. patent application Ser. No. 10/294,983, entitled "Artificial Intervertebral Disc Having A Captured Ball And Socket Joint With A Solid Ball And Retaining Cap" and filed Nov. 14, 2002; U.S. patent application Ser. No. 10/294,982, entitled "Artificial Intervertebral Disc" and filed Nov. 14, 2002; U.S. patent application Ser. No. 10/294,981, entitled "Artificial Intervertebral Disc Having A Captured Ball And Socket Joint With A Solid Ball And Compression Locking Post" and filed Nov. 14, 2002; U.S. patent application Ser. No. 10/642,523, entitled "Axially Compressible Artificial Intervertebral Disc Having Limited Rotation Using A Captured Ball and Socket" and filed Aug. 15, 2003; U.S. patent application Ser. No. 10/642,522, entitled Artificial Intervertebral Disc Having A Circumferentially Buried Wire Mesh Endplate Attachment Device and filed Aug. 15, 2003; U.S. patent application Ser. No. 11/073,987, entitled "Intervertebral Spacer Device Having A Circumferentially Buried Wire Mesh Endplate Attachment Device" and filed Aug. 15, 2003; U.S. patent application Ser. No. 10/642,526, entitled "Circumferentially Buried Wired Mesh Endplate Attachment Device For Use With An Orthopedic Device" and filed Aug. 15, 2003; U.S. patent application Ser. No. 10/294,984, entitled "Artificial Intervertebral Disc Having Limited Rotation Using A Captured Ball And Socket Joint With A Retaining Cap And A Solid Ball Having A Protrusion" and filed Nov. 14, 2002; U.S. patent application Ser. No. 10/294,985, entitled "Artificial Intervertebral Disc Having Limited Rotation Using A Captured Ball and Socket Joint With A Compression" and filed Ser. Nos. 10/294,985; 10/294,980, entitled "Artificial Intervertebral Disc Having Limited Rotation Using A Captured Ball And Socket Joint With A Solid Ball, A Retaining Cap, And An Interference Pin" and filed Nov. 14, 2002; U.S. patent application Ser. No. 10/294,986, entitled "Artificial Intervertebral Disc Having Limited Rotation Using A Captured Ball and Socket Joint With A Solid Ball, A Compression Locking Post, And An Interference Pin" and filed Nov. 14, 2002; U.S. patent application Ser. No. 10/282,356, entitled "Artificial Intervertebral Disc" and filed Sep. 26, 2002; U.S. patent application Ser. No. 10/784,646, entitled Artificial Intervertebral Disc Trial Having A Controllably Separable Distal End" and filed Feb. 23, 2004; U.S. patent application Ser. No. 10/309,585, entitled "Static Trials And Related Instruments and Methods For Use In Implanting An Artificial Intervertebral Disc" and filed Dec. 4, 2002; U.S. patent application Ser. No. 10/784,637, entitled "Instrumentation For Properly Seating An Artificial Disc In An Intervertebral Space" and filed Feb. 23, 2004; U.S. patent application Ser. No. 10/783,153, entitled "Parallel Distractor And Related Methods For Use In Implanting An Artificial Intervertebral Disc" and filed Feb. 20, 2004, the disclosures of which are hereby incorporated by reference herein.

BACKGROUND OF THE INVENTION

The present invention is directed to a spinal joint replacement implant and more particularly to a cervical intervertebral disc implant having saddle shaped articulating surfaces and to tooling and methods of inserting the cervical intervertebral disc implant.

As is well known to those skilled in the art, the structure of the intervertebral disc disposed between the cervical bones in the human spine comprises a peripheral fibrous shroud (the annulus) which circumscribes a spheroid of flexibly deformable material (the nucleus). The nucleus comprises a hydrophilic, elastomeric cartilaginous substance that cushions and supports the separation between the bones while also permitting articulation of the two vertebral bones relative to one another to the extent such articulation is allowed by the other soft tissue and bony structures surrounding the disc. The additional bony structures that define pathways of motion in various modes include the posterior joints (the facets) and the lateral intervertebral joints (the unco-vertebral joints). Soft tissue components, such as ligaments and tendons, constrain the overall segmental motion as well.

Traumatic, genetic, and long term wearing phenomena contribute to the degeneration of the nucleus in the human spine. This degeneration of this critical disc material, from the hydrated, elastomeric material that supports the separation and flexibility of the vertebral bones, to a flattened and inflexible state, has profound effects on the mobility (instability and limited ranges of appropriate motion) of the segment, and can cause significant pain to the individual suffering from the condition. Although the specific causes of pain in patients suffering from degenerative disc disease of the cervical spine have not been definitively established, it has been recognized that pain may be the result of neurological implications (nerve fibers being compressed) and/or the subsequent degeneration of the surrounding tissues (the arthritic degeneration of the facet joints) as a result of their being overloaded.

Traditionally, the treatment of choice for physicians caring for patients who suffer from significant degeneration of the cervical intervertebral disc is to remove some, or all, of the damaged disc. In instances in which a sufficient portion of the intervertebral disc material is removed, or in which much of the necessary spacing between the vertebrae has been lost (significant subsidence), restoration of the intervertebral separation is required.

Unfortunately, until the advent of spine arthroplasty devices, the only methods known to surgeons to maintain the necessary disc height necessitated the immobilization of the segment. Immobilization is generally achieved by attaching metal plates to the anterior or posterior elements of the cervical spine, and the insertion of some osteoconductive material (autograft, allograft, or other porous material) between the adjacent vertebrae of the segment. This immobilization and insertion of osteoconductive material has been utilized in pursuit of a fusion of the bones, which is a procedure carried out on tens of thousands of pain suffering patients per year.

This sacrifice of mobility at the immobilized, or fused, segment, however, is not without consequences. It was traditionally held that the patient's surrounding joint segments would accommodate any additional articulation demanded of them during normal motion by virtue of the fused segment's immobility. While this is true over the short-term (provided only one, or at most two, segments have been fused), the effects of this increased range of articulation demanded of these adjacent segments has recently become a concern. Specifically, an increase in the frequency of returning patients who suffer from degeneration at adjacent levels has been reported.

Whether this increase in adjacent level deterioration is truly associated with rigid fusion, or if it is simply a matter of the individual patient's predisposition to degeneration is unknown. Either way, however, it is clear that a progressive fusion of a long sequence of vertebrae is undesirable from the perspective of the patient's quality of life as well as from the perspective of pushing a patient to undergo multiple operative procedures.

While spine arthroplasty has been developing in theory over the past several decades, and has even seen a number of early attempts in the lumbar spine show promising results, it is only recently that arthroplasty of the spine has become a truly realizable promise. The field of spine arthroplasty has several classes of devices. The most popular among these are: (a) the nucleus replacements, which are characterized by a flexible container filled with an elastomeric material that can mimic the healthy nucleus; and (b) the total disc replacements, which are designed with rigid baseplates that house a mechanical articulating structure that attempts to mimic and promote the healthy segmental motion.

Among these solutions, the total disc replacements have begun to be regarded as the most probable long-term treatments for patients having moderate to severe lumbar disc degeneration. In the cervical spine, it is likely that these mechanical solutions will also become the treatment of choice. At present, there are two devices being tested clinically in humans for the indication of cervical disc degeneration. The first of these is the Bryan disc, disclosed in part in U.S. Pat. No. 6,001,130. The Bryan disc is comprised of a resilient nucleus body disposed in between concaval-covex upper and lower elements that retain the nucleus between adjacent vertebral bodies in the spine. The concaval-convex elements are L-shaped supports that have anterior wings that accept bones screws for securing to the adjacent vertebral bodies.

The second of these devices being clinically tested is the Bristol disc, disclosed substantially in U.S. Pat. No. 6,113,637. The Bristol disc is comprised of two L-shaped elements, with corresponding ones of the legs of each element being interposed between the vertebrae and in opposition to one another. The other of the two legs are disposed outside of the intervertebral space and include screw holes through which the elements may be secured to the corresponding vertebra; the superior element being secured to the upper vertebral body and the inferior element being attached to the lower vertebral body. The opposing portions of each of the elements comprise the articulating surfaces that include an elliptical channel formed in the lower element and a convex hemispherical structure disposed in the channel.

As is evident from the above descriptions, the centers of rotation for both of these devices, which are being clinically tested in human subjects, is disposed at some point in the disc space. More particularly with respect to the Bryan disc, the center of rotation is maintained at a central portion of the nucleus, and hence in the center of the disc space. The Bristol disc, as a function of its elongated channel (its elongated axis being oriented along the anterior to posterior direction), has a moving center of rotation which is at all times maintained within the disc space at the rotational center of the hemispherical ball (near the top of the upper element).

Thus, there remains a need for improved intervertebral discs, as well as new and improved methods for safely and efficiently implanting intervertebral discs.

SUMMARY OF THE INVENTION

Disclosed herein are intervertebral discs or implants, surgical instruments and procedures in accordance with certain preferred embodiments of the present invention. It is contemplated, however, that the implants, instruments and procedures may be slightly modified, and/or used in whole or in part and with or without other instruments or procedures, and still fall within the scope of the present invention. Although the present invention may discuss a series of steps in a procedure, the steps can be accomplished in a different order, or be used individually, or in subgroupings of any order, or in conjunction with other methods, without deviating from the scope of the invention.

In certain preferred embodiments of the present invention, an intervertebral disc implant includes a top element 102 and a bottom element 104. The top and bottom elements preferably have opposing articulating surfaces that engage one another. The intervertebral disc implant is adapted to be inserted into a disc space between adjacent vertebrae. In certain preferred embodiments, two or more disc implants can be stacked over one another in two or more successive disc spaces. In still other preferred embodiments, the disc implants are cervical implants.

The top element of the implant preferably includes a first bone engaging surface having a protrusion and a second articulating surface. The top element desirably includes a posterior end, an anterior end and an opening at the anterior end that is adapted to receive a prong or post of an insertion instrument. The top element desirably includes opposing lateral sides that extend between the posterior end and the anterior end of the top element. In certain preferred embodiments, the intervertebral disc implant may be at least partially coated with an osteoconductive material to facilitate long-term fixation to endplates of vertebral bodies.

The articulating surface of the top element preferably defines a convex curve or surface extending between the sides. The articulating surface also defines a concave curve or surface extending between the posterior and anterior ends of the top element. In certain preferred embodiments, the articulating surface defines a toroidal saddle-shaped surface.

The protrusions on the top element preferably include teeth 122, which desirably have sloping surfaces. Each of the sloping surfaces preferably has a low point nearer to the posterior end of the top element and a high point nearer to the anterior end of the top element. The sloping surfaces preferably facilitate insertion of the posterior end of the top element into a disc space while making it more difficult for the top element to be removed or discharged from the disc space in a posterior to anterior direction.

The intervertebral disc implant preferably includes the bottom element having a first bone engaging surface and a second articulating surface that is designed to engage the articulating surface of the top element when the top and bottom elements contact one another. The bottom element includes a posterior end, an anterior end, and lateral sides extending between the posterior end and the anterior end. The first bone engaging surface of the second element includes first and second protrusions, with each protrusion preferably including teeth. The teeth desirably include sloping surfaces having a low point nearer to the posterior end of the bottom element and a high point nearer to the anterior end of the bottom element. The sloping surfaces on the teeth of the bottom element preferably facilitate insertion of the bottom element into a disc space. The teeth have vertical surfaces, however, that hinder or prevent dislodgement of the implant from the disc space. In certain preferred embodiments, the teeth on the top and bottom elements may have the same structure, or one or more features of the teeth described above.

The bottom element desirably has two openings provided at the anterior end thereof. The two openings are preferably adapted to receive the prongs or pins of an insertion instrument, as will be described in more detail below. In certain preferred embodiments, the bottom element may be at least partially coated with an osteoconductive material to facilitate long-term fixation to a vertebral endplate.

The articulating surface of the bottom element preferably defines a convex curve or surface extending between the posterior end and the anterior end of the bottom element. The articulating surface preferably defines a concave curve or surface extending between the lateral sides of the bottom element. As will be described in more detail herein, the articulating surface preferably defines a toroidal saddle-shaped surface that engages the articulating surface of the top element when the top end bottom elements are in contact with one another.

When the top element is assembled with the bottom element, the opposing articulating surfaces are adapted to engage one another. When the top and bottom elements are assembled together, the projection on the top element is offset from the two projections on the bottom element. In prior art devices, it has been observed that stacking two implants in successive disc spaces may result in cracking of vertebral bone between the implants because the apexes on the teeth of the two implants are in alignment. The present invention seeks to avoid this cracking problem by offsetting the projection on the top element from the projections on the bottom element. Although the present invention is not limited by any particular theory of operation, it is believed that providing projections that are offset from one another enables two or more intervertebral disc implants to be inserted into two or more successive disc spaces, while minimizing the likelihood of cracking the vertebral bodies between the disc spaces.

Prior to insertion into an intervertebral space, the articulating surface of the top element opposes the articulating surface of the bottom element. In preferred embodiments, the articulating surface of the top element defines a toroidal saddle-shaped surface including a concave surface extending between proximal and anterior ends thereof and a convex surface extending between the sides of the top element. The articulating surface of the bottom element also preferably includes a toroidal saddle-shaped surface having a convex surface extending between the posterior and anterior ends and a concave surface extending between the sides of the bottom element. The articulating surfaces may be similar to the articulating surfaces disclosed in commonly assigned U.S. Pat. No. 6,997,955, the disclosure of which is hereby incorporated by reference herein.

In other preferred embodiments of the present invention, a kit for preparing an intervertebral disc space for receiving an implant includes a plurality of trials having different sizes. Each trial preferably includes a body insertible into an intervertebral disc space, the body having a leading end, a trailing end, a top surface with a first groove formed therein and a bottom surface with a second groove formed therein. The grooves preferably extend between the leading and trailing ends of the body. Each trial also desirably includes a flange secured to the trailing end of the body, the flange having a first channel aligned with the first groove and a second channel aligned with the second groove, wherein each of the different sized trials has a different flange thickness. Although the present invention is not limited by any particular theory of operation, it is believed that changing the flange thickness will limit the depth to which bone cutting instruments such as a chisel may be advanced into vertebral bone. Thus, in certain preferred embodiments, a smaller sized trial will have a thicker flange and a larger sized trial will have a thinner flange.

In certain preferred embodiments, the top surface of the body desirably tapers toward the bottom surface of the body between the trailing end and the leading end of the body. In other words, the leading end of the body has a taper which facilitates insertion into a disc space.

The trial desirably includes a third groove formed in the bottom surface of the body, wherein the first groove is offset from the second and third grooves, and the second and third grooves are spaced from one another. The flange preferably includes a third channel aligned with the third groove in the body.

In preferred embodiments, the first channel has an upper end having a first width and a lower end having a second width that is less than the first width. The first groove in the body preferably has a width that is substantially the same as the first width of the first channel. The second channel desirably has a lower end having a first width and an upper end having a second width that is less than the first width of the second channel. The second groove in the body desirably has a width that is substantially the same as the first width of said second channel.

In another preferred embodiment of the present invention, an inserter head for an intervertebral disc implant includes a body having a leading end with a concave surface, whereby the concave surface has an upper end and a lower end. The inserted head preferably includes a first pin projecting from the concave surface adjacent the upper end of the concave surface, and a pair of second pins spaced from one another and projecting from the concave surface adjacent the lower end of the concave surface. The first pin may be resilient. The inserter head desirably includes a wedge projecting from the concave surface and being disposed between the first pin and the pair of second pins.

The inserter head desirably includes a first flange projecting upwardly from the body and a second flange projecting downwardly from the body. The first and second flanges are desirably adapted for engaging vertebral bone for limiting advancement of the inserter head into an intervertebral disc space. The inserter head may desirably include a stem projecting from a trailing end of the inserter head for coupling the inserter head to a handle.

In further preferred embodiments of the present invention, a combination inserter head and intervertebral disc implant includes the intervertebral disc implant having a top element with a posterior end, an anterior end, an opening in the anterior end, a bone engaging surface and an articulating surface. The intervertebral disc implant preferably has a bottom element with a posterior end, an anterior end, a pair of spaced openings in the anterior end, a bone engaging surface and an articulating surface that opposes the articulating surface of the top element.

In the combination, the inserter head preferably includes a body having a leading end with a concave surface, the concave surface having an upper end and a lower end. The inserter head desirably has a first pin, such as a resilient pin, projecting from the concave surface adjacent the upper end of the concave surface, a pair of second pins spaced from one another and projecting from the concave surface adjacent the lower end of the concave surface, and a wedge projecting from the concave surface and being disposed between the first pin and the pair of second pins. The first pin is disposed in the opening of the top element of the implant and the pair of second pins are disposed in the pair of openings in the bottom element of the implant.

As noted above, the first pin is preferably resilient for urging the top element of the implant against the wedge of the inserter head. The pair of spaced second pins on the inserter head are desirably spaced from one another by a first distance and the pair of openings in the lower element of the implant are spaced from one another by a second distance that is different than the first distance. In certain preferred embodiments, the first distance is greater than the second distance. In other preferred embodiments, however, the first distance is less than the second distance. The different distances preferably form a friction lock between the pair of pins and the pair of openings in the bottom element.

In still other preferred embodiments of the present invention, a kit for stabilizing a spinal segment includes a plurality of two-part intervertebral disc implants having different sizes and a plurality of inserter heads having different sizes, whereby each of the inserter heads is adapted for holding together one of the two-part intervertebral disc implants as a single implantable unit.

The inserter head may have indicia corresponding to the size of the intervertebral disc implant held by the inserter head. The indicia may include a color code and/or text indicating the size of the intervertebral disc implant held by the inserter head.

Each intervertebral disc implant preferably has a top element including a bone engaging surface, an articulating surface and an opening at an anterior end thereof, and a bottom element including a bone engaging surface, an articulating surface and a pair of openings adjacent the anterior end thereof, whereby the inserter head includes pins insertible into the openings at the anterior end for holding the articulating surfaces of the top and bottom elements in contact with one another.

In certain preferred embodiments, the intervertebral disc implant, or the instruments, may alternatively or additionally incorporate any or all of the features discussed previously, disclosed herein, or discussed in U.S. patents and/or patent applications incorporated by reference herein. Preferably, the configuration of the bearing surfaces of the intervertebral disc implant in this preferred embodiment may be substantially similar to those of the other bearing surface configurations discussed previously, disclosed herein, or incorporated by reference herein.

It should be noted that features and methods and functionalities of the present invention, including but not limited to features and methods and functionalities for engaging one tool (or parts thereof) with one or more other tools (or parts thereof) or with the implants (or parts thereof), and vice-versa; for addressing, avoiding, manipulating, or engaging the patient's anatomy; for aligning one or more tools with anatomic or non-anatomic reference points; and for aligning the tools and implants with one another and/or a treatment space; are not and should not be limited to those embodied in and achieved by the structures and methods of the specific embodiments described and shown, but rather the structures and methods of the specific embodiments described and shown are merely examples of structures and methods that can achieve certain features and methods and functionalities of the present invention.

Another aspect of the present invention includes a method of performing spinal surgery including the steps of inserting a trial in an intervertebral disc space between two adjacent vertebrae, cutting a portion of at least one vertebrae while the trial is in the intervertebral disc space, removing the trial, and inserting a two-part intervertebral disc implant in the intervertebral disc space. The method may further include the step of attaching the two-part intervertebral disc implant to an inserter head having a size corresponding to the implant.

These and other preferred embodiments of the present invention will be described in more detail below.

BRIEF DESCRIPTION OF THE DRAWINGS

FIGS. 2A-2G show the top element of the intervertebral disc implant shown in FIGS. 1A and 1B.

FIGS. 3A-3G show the bottom element of the intervertebral disc implant shown in FIGS. 1A and 1B.

FIGS. 4A-4C show a combination trial and chisel guide used for preparing an intervertebral disc space for receiving the intervertebral disc implant shown in FIGS. 1A and 1B, in accordance with certain preferred embodiments of the present invention.

FIGS. 5A-5D show a chisel used with the combination trial and chisel guide of FIGS. 4A-4C, in accordance with certain preferred embodiments of the present invention.

FIGS. 6A-6E show the chisel of FIGS. 5A-5D assembled with the combination trial and chisel guide of FIGS. 4A-4C.

FIGS. 9A-9D show a handle attachable to the combination trial and chisel guide of FIGS. 4A-4C and the inserter head of FIGS. 7A-7C, in accordance with certain preferred embodiments of the present invention.

FIG. 10 shows a pusher rod, in accordance with certain preferred embodiments of the present invention.

FIGS. 12A-12C show the pusher rod of FIG. 10 coupled with the handle of FIGS. 9A-9C.

FIG. 15 shows a combination trial and chisel guide, in accordance with still another preferred embodiment of the present FIG. 16 shows a combination trial and chisel guide, in accordance with yet a further preferred embodiment of the present invention.

DETAILED DESCRIPTION

Figure 1A:
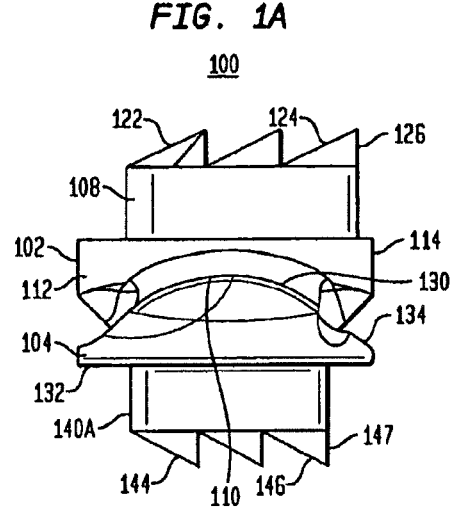
FIG. 1A shows a side elevational view of an intervertebral disc implant having a top element and a bottom element, in accordance with certain preferred embodiments of the present invention.
Figure 1B:
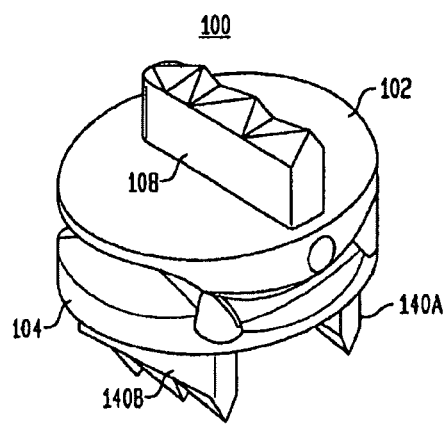
FIG. 1B shows a perspective view of the intervertebral disc implant shown in FIG. 1A.

Referring to FIGS. 1A and 1B, in certain preferred embodiments of the present invention, an intervertebral disc implant 100 includes a top element 102 and a bottom element 104. As will be described in more detail below, the top and bottom elements 102, 104 have opposing articulating surfaces that engage one another. The intervertebral disc implant is adapted to be inserted into a disc space between adjacent vertebrae. In certain preferred embodiments, two or more disc implants can be stacked over one another in two or more successive disc spaces. In still other preferred embodiments, the disc implants are cervical implants.

Referring to FIGS. 2A-2E, the top element 102 includes a first bone engaging surface 106 having a protrusion 108 and a second articulating surface 110. Referring to FIGS. 2E-2G, the top element 102 has a posterior end 112 and an anterior end 114. As shown in FIGS. 2A-2B and 2D, the top element 102 has an opening 116 at the anterior end 114 thereof that is adapted to receive a prong or post of an insertion instrument, as will be described in more detail below. Referring to FIGS. 2C-2D and 2F-2G, the top element 102 has opposing lateral sides 118, 120 that extend between the posterior end 112 and the anterior end 114 of the top element. In certain preferred embodiments, the intervertebral disc implant may be at least partially coated with an osteoconductive material to facilitate long-term fixation to endplates of vertebral bodies.

Referring to FIGS. 2C and 2D, the articulating surface 110 preferably defines a convex curve or surface extending between the sides 118, 120 of the top element 102. Referring to FIGS. 2A and 2E, the articulating surface 110 also defines a concave curve or surface extending between the posterior and anterior ends 112, 114 of the top element 102. In certain preferred embodiments, the articulating surface 110 defines a toroidal saddle-shaped surface.

As shown in FIGS. 2A-2E and 2G, the protrusion 108 preferably includes teeth 122. Referring to FIG. 2E, the teeth 122 desirably have sloping surfaces 124, each sloping surface preferably having a low point nearer to the posterior end 112 of the top element 102 and a high point nearer to the anterior end 114 of the top element 102. Referring to FIGS. 2E and 2G, the sloping surfaces 124 preferably facilitate insertion of the posterior end 112 of the top element 102 into a disc space while making it more difficult for the top element to be removed or discharged from the disc space. Thus, referring to FIG. 2G, the sloping surfaces 124 of the teeth 122 facilitate insertion of the implant in a direction indicated by arrow $D_1$, while the vertical surfaces 126 (FIG. 2E) of the teeth 122 hinder or prevent dislodgement of the implant in the direction indicated by arrow $D_2$.

Referring to FIGS. 3A-3E, the intervertebral disc implant preferably includes the bottom element 104 having a first bone engaging surface 128 and a second articulating surface 130 that is designed to engage the articulating surface 110 of the top element 102 (FIG. 2A) when the top and bottom elements contact one another. The bottom element 104 includes a posterior end 132, an anterior end 134, and lateral sides 136, 138 extending between the posterior end and the anterior end. Referring to FIGS. 3C-3D and 3G, the first bone engaging surface 128 of the second element includes first and second protrusions 140A, 140B, with each protrusion 140A, 140B preferably including teeth 144. Referring to FIGS. 3E and 3G, the teeth include sloping surfaces 146 having a low point nearer to the posterior end 132 of the bottom element 104 and a high point nearer to the anterior end 134 of the bottom element 104. Referring to FIG. 3G, similar to the sloping surfaces 146 of the teeth of the top element 102 described above, the sloping surfaces 146 on the teeth 144 facilitate insertion of the bottom element 104 in the direction indicated by arrow $D_3$. The teeth 144 have vertical surfaces 147, however, that hinder or prevent dislodgement of the implant in the direction indicated by arrow $D_4$.

Referring to FIGS. 3A-3B, 3D and 3F, the bottom element 108 has two openings 150A, 150B provided at the anterior end 134 thereof. The openings 150A, 150B are preferably adapted to receive the prongs of an insertion instrument, as will be described in more detail below. In certain preferred embodiments, the bottom element 104 may be at least partially coated with an osteoconductive material to facilitate long-term fixation to a vertebral endplate.

Referring to FIGS. 3A and 3E, the articulating surface 130 preferably defines a convex curve or surface extending between the posterior end 132 and the anterior end 134 of the bottom element 104. Referring to FIGS. 3C and 3D, the articulating surface 130 preferably defines a concave curve or surface extending between the lateral sides 136, 138 of the bottom element 104. As will be described in more detail herein, the articulating surface 130 preferably defines a toroidal saddle-shaped surface that engages the articulating surface 110 of the top element 102 (FIG. 2A) when the top end bottom elements are in contact with one another.

FIGS. 1A and 1B show the top element 102 of FIG. 2A being assembled with the bottom element 104 of FIG. 3A. The opposing articulating surfaces 110, 130 of the respective top element 102 and the bottom element 104 are adapted to engage one another. The teeth 122 on the top element 102 slope downwardly toward the posterior end 112 of the top element. Similarly, the teeth 144 on the bottom element 104 slope downwardly toward the posterior end 132 of the bottom element.

Referring to FIG. 1B, when the top and bottom elements 102, 104 are assembled together, the projection 108 on the top element 102 is offset from the two projections 140A, 140B on the bottom element 104. In prior art devices, it has been observed that stacking two implants in successive disc spaces may result in cracking of vertebral bone between the implants because the apexes on the teeth of the two implants are in alignment. The present invention seeks to avoid this cracking problem by offsetting the projection 108 on the top element 102 from the projections 140A, 140B on the bottom element 104. Although the present invention is not limited by any particular theory of operation, it is believed that providing projections 108, 140 that are offset from one another enables two or more intervertebral disc implants to be inserted into two or more successive disc spaces, while minimizing the likelihood of cracking the vertebral bodies between the disc spaces.

Referring to FIGS. 1A-1B, in preferred embodiments of the present invention, prior to insertion into an intervertebral space, the articulating surface 110 of the top element 102 opposes the articulating surface 130 of the bottom element 104. In preferred embodiments, the articulating surface 110 of the top element 102 defines a toroidal saddle-shaped surface including a concave surface extending between proximal and anterior ends 112, 114 thereof and a convex surface extending between the sides 118, 120 of the top element 102. The articulating surface 130 of the bottom element 104 also preferably includes a toroidal saddle-shaped surface having a convex surface extending between the posterior and anterior ends 132, 134 and a concave surface extending between the sides 136, 138 of the bottom element 104.

The articulating surfaces may be similar to the articulating surfaces disclosed in commonly assigned U.S. Pat. No. 6,997,955, the disclosure of which is hereby incorporated by reference herein. In certain preferred embodiments of the present invention, the longitudinally inwardly directed articulation surface of the top element 102 forms a constant radii saddle-shaped articulation surface. More particularly, the saddle surface is defined by a concave arc that is swept perpendicular to and along a convex arc. The articulation surface has a cross-section in one plane that forms a concave arc, and a cross-section in another plane (perpendicular to that plane) that forms a convex arc. The concave arc has a respective constant radius of curvature about an axis perpendicular to the one plane. The convex arc has a respective constant radius of curvature about an axis perpendicular to the other plane.

In a preferred embodiment, the concave arc has a constant radius of curvature A about an axis perpendicular to the anterior-posterior plane, and the convex arc has a constant radius of curvature B about an axis perpendicular to the lateral plane. Preferably, radius A is less than radius B.

The longitudinally inwardly directed articulation surface of the bottom element 104 also preferably forms a constant radii saddle-shaped articulation surface. More particularly, the saddle-shaped surface is defined by a convex arc that is swept perpendicular to and along a concave arc. The articulation surface has a cross-section in one plane that forms a convex arc, and a cross-section in another plane (perpendicular to that plane) that forms a concave arc. The convex arc has a respective constant radius of curvature about an axis perpendicular to the one plane. The concave arc has a respective constant radius of curvature about an axis perpendicular to the other plane.

In a preferred embodiment, the convex arc has a constant radius of curvature C about an axis perpendicular to the anterior-posterior plane, and the concave arc has a constant radius of curvature D about an axis perpendicular to the lateral plane. Preferably, radius C is less than radius D.

The constant radii saddle shaped articulation surfaces of the top and bottom elements are configured and sized to be nestable against one another and articulatable against one another, to enable adjacent vertebral bones (against which the top and bottom elements are respectively disposed in the intervertebral space) to articulate in flexion, extension, and lateral bending. More particularly, the intervertebral disc of the present invention is assembled by disposing the top and bottom elements so that the vertebral body contact surfaces are directed away from one another, and the articulation surfaces are nested against one another such that the concave arcs accommodate the convex arcs.

Accordingly, movement of the adjacent vertebral bones relative to one another is permitted by the movement of the top and bottom elements relative to one another. In flexion and extension, the concave arcs of the top element 102 ride on the convex arcs of the bottom element 104 about a center of rotation below the articulation surfaces. In lateral bending, the concave arcs of the bottom element 104 ride on the convex arcs of the top element 102 about a center of rotation above the articulation surfaces. During these articulations, the elements are maintained at constant relative distraction positions, i.e., the elements do not move in directions that are directed away from one another (for example, do not move in opposing axial directions from one another (e.g., along a longitudinal axis of the spine)). Accordingly, in certain preferred embodiments, the present invention provides a pair of articulation surfaces that have a center of rotation above the surfaces in one mode of motion (e.g., lateral bending), and a center or rotation below the surfaces in another (e.g., flexion/extension), consistent in these regards with the motion of a natural intervertebral joint, such as a cervical joint. Preferably, the articulation surfaces are sized and configured so that the respective ranges of angles through which flexion/extension and lateral bending can be experienced are equal to or greater than the respective normal physiologic ranges for such movements in the cervical spine.

It is preferable that, in addition to the flexion, extension, and lateral bending motions described above, the adjacent vertebral bones be permitted by the intervertebral disc implant to axially rotate relative to one another (e.g., about the longitudinal axis of the spinal column) through a small range of angles without moving in opposite (or otherwise directed away from one another) directions (e.g., along the longitudinal axis) within that range, and then to engage in such opposite (or otherwise directed away from one another) movement once that range is exceeded. Preferably, the articulation surfaces are accordingly configured and sized to permit such movements. Because of the differing radii of the opposing articulation surfaces, the top and bottom elements are able to axially rotate relative to one another about the longitudinal axis of the spinal column through a range of angles without causing the vertebral body contact surfaces to move away from one another along the longitudinal axis. Once the axial rotation exceeds that range, however, the articulation surfaces interfere with one another as the concave arcs move toward positions in which they would be parallel to one another, and the distance between the vertebral body contact surfaces increases with continued axial rotation as the concave arcs ride up against their oppositely directed slopes. Thus, the articulation surfaces are configurable according to the present invention to permit normal physiologic axial rotational motion of the adjacent vertebral bones about the longitudinal axis through a range of angles without abnormal immediate axially opposite (or otherwise directed away from one another) movement, and to permit such axially opposite (or otherwise directed away from one another) movement when under normal physiologic conditions it should occur, that is, outside that range of angles.

The articulation surfaces preferably maintain contact over a range of normal physiologic articulating movement between the adjacent vertebral bones. That is, through flexion, extension, lateral bending, and axial rotation, the articulation surfaces are in contact with one another. Preferably, the surface area dimensions of the articulation surfaces are selected in view of the selected radii of curvature to prevent the edges of the saddle surfaces (particularly the edges of the concave arcs) from hitting any surrounding anatomic structures, or other portions of the opposing upper or lower element, before the limit of the normal physiologic range of an attempted articulation is reached.

Referring to FIGS. 1A and 1B, the intervertebral disc implant 100 includes the top element 102 and the bottom element 104. The articulating surface of the top element 102 preferably engages the articulating surface of the bottom element 104. The articulating surface of the top element 102 defines a convex surface extending between lateral sides 118, 120 thereof and the articulating surface of the bottom element 104 defines a concave surface extending between the lateral sides 136, 138 thereof. After the opposing articulating surfaces are in contact with one another, the protrusion 108 on the top element 102 is offset from the protrusion 140A, 140B on the bottom element 104. The offset protrusions preferably permit stacking of two intervertebral disc implants in two successive disc spaces, while minimizing the likelihood of cracking the vertebral bone between the adjacent disc spaces. In other preferred embodiments, the offset protrusions enable three or more intervertebral discs to be stacked atop one another over three or more successive disc spaces.

Referring to FIG. 1B, the articulating surface 110 of the top element 102 defines a concave surface extending between posterior 112 and anterior 114 ends thereof. The articulating surface 130 of the bottom element 104 defines a convex surface extending between the posterior 132 and anterior 134 ends thereof. The teeth 122 on the protrusion 108 of the top element 102 include sloping surfaces 124 that slope downwardly toward the posterior end 112 of the top element 102. The teeth 144 on the protrusions 140A, 140B of the bottom element 104 have sloping surfaces 146 that slope downwardly toward the posterior end 132 of the bottom element 104. As a result, the sloping surfaces 124, 146 of the respective teeth 122, 144 slope in the same direction, i.e., toward the posterior ends of the top and bottom elements 102, 104. The respective sloping surfaces 124, 146 facilitate insertion of the implant 100 into a disc space. The vertical surfaces 126, 147 on the respective teeth 122, 144, however, hinder or prevent expulsion or migration of the implant 100 from the disc space after it has been inserted.

FIGS. 4A-4C show a combination trial and chisel guide 152, in accordance with certain preferred embodiments of the present invention. Referring to FIG. 4B, the trial 152 includes a body 154 having a top surface 156 with a leading end 158 that is sloped and a bottom surface 160. The trial body 154 also includes a leading end 162 designed for insertion into a disc space and a trailing end 164. The trial includes a flange 166 connected with the trailing end 164 of the body 154. The flange 166 includes an upper flange 168 that projects above top surface 156 of the body 154 and a bottom flange section 170 that projects below the bottom surface 160 of the body 154. The trailing end 164 of the body 154 includes a stem 172 projecting therefrom. The stem 172 includes a tapered section 174 that engages an end of a handle, as will be described in more detail below.

Referring to FIG. 4A, the body 154 preferably includes a groove 176 formed in the top surface 156 thereof. The groove 176 extends from the leading end 162 of the body toward the flange 166 at the trailing end of the body. The groove 176 guides advancement of a cutting blade on a chisel for forming an opening in an end plate of a vertebral body to accept the protrusion 108 of the top element 102, as will be described in more detail below. In certain preferred embodiments of the present invention, it is contemplated that a chisel, broach or other cutting instrument may be used for forming the openings. A chisel typically has cutting edges along its axis. A chisel typically has just a single cutting edge. As used herein, the term chisel is deemed to cover both a chisel and a broach, or any other cutting tool that may be used to cut bone. The bottom surface of the body 154 preferably includes a pair of grooves (FIG. 6B) that are offset from the single groove 176 provided in the top surface 156 of the body 154. The two grooves at the bottom of the body guide advancement of respective cutting blades on a chisel for forming openings in a second vertebral body that opposes the first vertebral body to accept protrusions 140A and 140B of the bottom element 104. Thus, the trial and chisel guide can be used for forming openings in opposing vertebrae.

FIG. 4C shows a rear elevational view of the trial and chisel guide shown in FIGS. 4A and 4B. The upper flange portion 168 includes openings 178A, 178B that are adapted to receive anchoring elements such as pins or screws for temporarily securing the flange to bone. The upper flange portion 168 also includes a channel 180 having a wider upper end 182 and a narrower lower end 184. The lower flange portion 170 includes a pair of channels 186A, 186B. The first channel 186A in the lower flange portion 170 has a wider section 188A that becomes narrower at an upper end 190A thereof. The lower flange section 170 also includes the second channel 186B having a lower end 188B that is wider in an upper end 190B that is narrower. The cutting blades on the chisel pass through the wider upper ends 182, 188A and 188B of the channels. The cutting blades of the chisel are too wide to pass through the narrow sections 184, 190A and 190B of the channels. The narrow sections 184, 190A and 190B of the channels provide a relief for cut bone chips and particles to escape.

As shown in FIG. 4C, the channel 180 in the upper flange part 168 is offset from the two channels 186A, 186B in the lower flange portion 170. The respective channels 180, 186A, 186B are aligned with the respective grooves formed in the upper and lower surfaces of the body of the trial 154.

Referring to FIGS. 4A and 4B, in certain preferred embodiments of the present invention, a plurality of trial and chisel guides having different sizes are provided in a kit. The different sized trials are used to determine the correct size for an intervertebral disc implant to be placed in a disc space. Each of the trial and chisel guides may have a body having a different size. The differently sized bodies of the trials may have a different width, height and/or depth. In addition, the thickness of the flange 166 for the trial may vary. Although the present invention is not limited by any particular theory of operation, it is believed that the thickness of the flange will control how far the cutting blades on a chisel may advance into the grooves on a trial body for controlling the depth of cutting into the vertebral bodies.

FIGS. 5A-5C show a chisel 192 used for forming openings in opposing vertebral bodies that accept the protrusions of the top element 102 and the bottom element 104, in accordance with certain preferred embodiments of the present invention. Referring to FIGS. 5B and 5C, the chisel 192 includes a leading end 194 and a trailing end 196. The chisel includes a handle 198 extending between the leading and trailing ends and a striking surface 200 provided at the trailing end. As will be described in more detail below, after the chisel is assembled with the trial, a hammer, mallet or other similar instrument may be struck against the striking surface 200 for advancing the chisel through the grooves in the body of the trial and into vertebral bone.

Referring to FIG. 5A, the leading end 194 of the chisel 192 includes a first cutting blade 202 adapted to form an opening in a first vertebral body and second cutting blades 204A, 204B for forming openings in a second vertebral body. Referring to FIG. 5B, the chisel includes a notch 206 provided near the leading end thereof that is adapted to accommodate the base 173 of the stem 172 (FIG. 4A) of the trial. When the chisel 192 is assembled with the trial 154 (FIG. 4A), the first cutting blade slides in the groove provided in the upper surface of the trial and the second cutting blades 204 slide in the grooves provided in the bottom surface of the trial. Referring to FIGS. 5C and 5D, the first cutting blade 202 of the chisel is offset from the pair of second cutting blades 204A, 204B.

FIGS. 6A-6E show the chisel 192 of FIG. 5A being assembled with the trial 154 of FIG. 4A. As shown in FIG. 6A, the first cutting blade 202 slides through channel 180 and groove 176 for cutting a first keel opening in an end face of a first vertebral body. Referring to FIGS. 6A and 6B, the pair of second cutting blades 204A, 204B pass through channels 186A, 186B of lower flange portion 170 and through grooves (not shown) provided in the bottom surface 160 of the trial.

FIG. 6D shows the pair of second cutting blades 204A, 204B extended over the bottom surface of the trial and first cutting blade 202 extending over the top surface of the trial.

In one preferred embodiment of the present invention, a surgeon selects one of the combination trial and chisel guides from a kit. After the trial and chisel guide is attached to a distal end of a handle (FIGS. 9A and 9B), the surgeon inserts the body of the trial into the disc space and observes and senses whether the selected trial is the correct size. If the trial is not the correct size, then the surgeon will select a trial having a different size and insert that trial into the disc space. The surgeon will continue to evaluate trials having different sizes until a correctly sized trial has been identified. At that point, the surgeon will note the size of the trial and will use the size information for selecting an appropriately sized chisel and intervertebral disc implant.

The surgeon will then use the correctly sized trial to form the openings in the opposing faces of the vertebral bodies. While maintaining the body of the trial in the disc space, the surgeon will secure the flange 166 to bone by passing pins or screws through the openings 178A, 178B in the flange (FIG. 4C). The chisel 192 shown in FIGS. 5A-5D will then be assembled with the trial so that the cutting blades are advanceable in the grooves in the body of the trial. A mallet or hammer may be used for driving the cutting blades into the vertebral bodies for forming the above-discussed openings for accepting the protrusions of the top and bottom portions, 102 and 104, respectively.

In certain preferred embodiments, a plurality of combination trial and chisel guides of different sizes are provided. The bodies of the trial and chisel guides may have different sizes, heights, lengths and/or widths. The flanges provided at the trailing ends of the bodies may also have different thicknesses. In further preferred embodiments, a plurality of chisels are provided, each chisel being size specific to the trial selected. Thus, the prongs of a first chisel may be longer than the prongs of a second chisel so that the respective chisels cut channels in bone having different lengths.

Figure 7A:
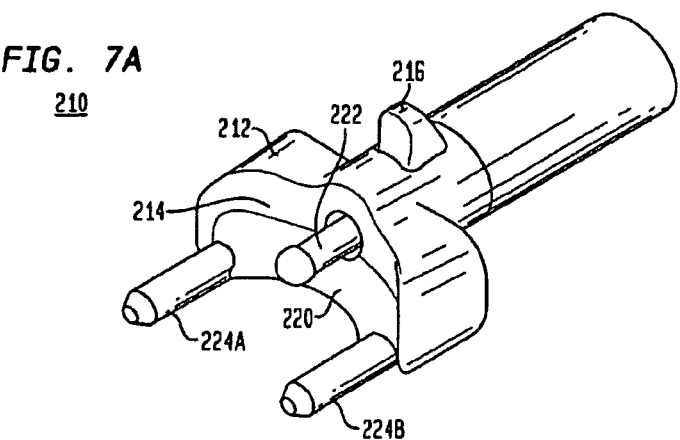
FIGS. 7A-7C show an inserter head for inserting the intervertebral disc implant of FIGS. 1A-1B into an intervertebral disc space, in accordance with certain preferred embodiments of the present invention.
Figure 7B:
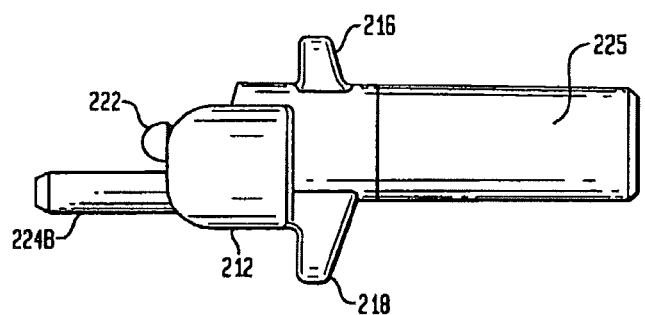
Figure 7C:
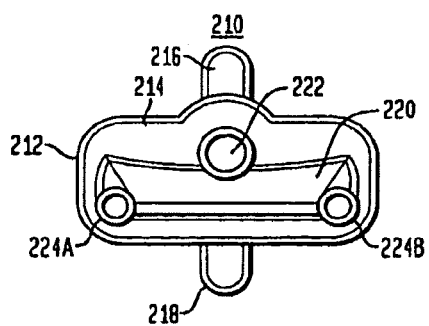

FIGS. 7A-7C show an inserter head 210 used for inserting an intervertebral disc implant into a disc space, in accordance with certain preferred embodiments of the present invention. Referring to FIG. 7A, the inserter head 210 preferably includes a body 212 having a concave surface 214 at a leading end thereof. Referring to FIGS. 7A and 7B, the body 212 preferably includes a top flange 216 projecting from an upper end thereof and a bottom flange 218 projecting from a lower end thereof. The flanges 216, 218 limit advancement of the inserter head 210 into an intervertebral disc space. The body 212 includes a wedge 220 having a sloping surface. In addition, the leading end of the body 212 includes a first pin 222 adapted to engage the opening in the top element of the intervertebral disc implant (FIG. 1A). The first pin 222 is preferably resilient. When the first pin 222 is inserted into the opening 116 in the top element 102 of the implant (FIG. 2B), the resilient pin 222 presses the articulating surface 110 of the top element against the sloping surface 220 of the wedge 220.

The leading end of the body of the inserted head also preferably includes a pair of second pins 224A, 224B that are adapted to engage the pair of openings 150A, 150B in the bottom element 104 of the intervertebral disc implant (FIG. 3D). The distance between the second pins 224A, 224B preferably defines a distance that is different than the distance between the openings 150A, 150B in the bottom element on the implant. In one preferred embodiment, the distance between the pins is slightly wider than the distance between the openings 150A, 150B. In another preferred embodiment, the distance between the pins is slightly narrower than the distance between the openings 150A, 150B. These differences preferably form a friction lock between the second pins 224A, 224B and the openings 150A, 150B (FIG. 3D) in the bottom element. The inserter head preferably has a tapered stem 225 at a trailing end thereof that is adapted to be received in a tapered opening at a leading end of a handle, as will be described in more detail below.

Figure 8A:
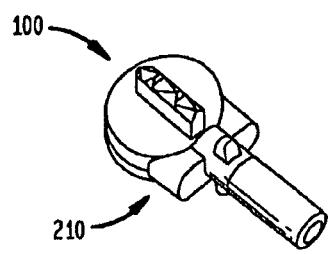
FIGS. 8A-8F show the inserter head of FIGS. 7A-7C coupled with the intervertebral disc implant of FIGS. 1A-1B.
Figure 8B:
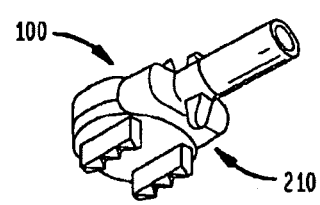
Figure 8E:
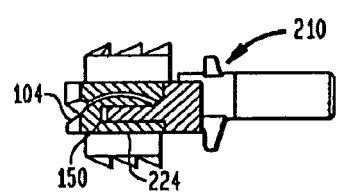
Figure 8D:
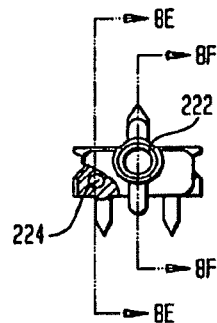
Figure 8F:
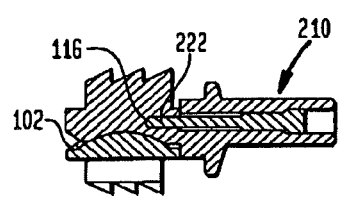
Figure 8C:
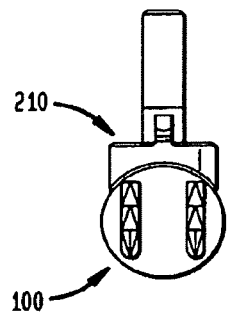

Referring to FIGS. 8A-8C, the inserter head 210 is adapted to secure the top and bottom elements of the intervertebral disc implant 100. Referring to FIGS. 8D and 8E, the bottom pins 224 of the inserter head 210 slide into the openings 150 in the bottom element 104 of the implant. Referring to FIGS. 8D and 8F, the first resilient pin 222 on the inserted head 210 slides into the opening 116 in the top element 102 of the implant. The first resilient pin urges the articulating surface of the top element against the wedge for securing the top element to the inserted head.

FIGS. 9A-9D show a handle 230 having a leading end 232, a trailing end 234 and a shaft 236 that extends between the leading and trailing ends. The leading end 232 of the shaft 236 includes a slot 238 formed therein that enables the leading end of the shaft to flex outwardly. Referring to FIG. 9B, the leading end 232 of the shaft 236 also includes a notch 240 that is adapted to slide over the flanges 216, 218 of the inserter head 210 (FIG. 7B) when the handle is assemble with the inserter head. Referring to FIG. 9D, the handle 230 has an opening 239 at the leading end that is tapered. The tapered opening 239 of the handle preferably accommodates the tapered stem 225 of the inserter head 210 (FIG. 7B). The tapered opening 239 of the handle 230 may also accommodate tapered stems on the plurality of combination trial and chisel guides (FIG. 4A). Referring to FIGS. 9A-9C, the trailing end 234 of the handle 230 includes a striking surface 240 that may be struck with a hammer or mallet for advancing the leading end 232 of the handle 230 toward an intervertebral disc space. The shaft 236 preferably has an opening that extends along the length thereof from the leading end 232 to the trailing end 234.

In certain preferred embodiments of the present invention, a pusher rod 244 includes a shaft 246 having a leading end 248 and a trailing end 250. The trailing end 250 of the shaft 246 includes a radially extending flange 252 having a striking surface 254. The shaft 246 preferably slides within the opening of the handle 230 (FIG. 9A).

Figure 11B:
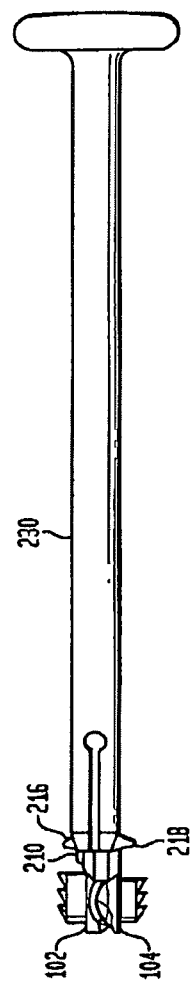
FIGS. 11A-11C show the handle of FIGS. 9A-9C attached to the inserter head of FIGS. 7A-7C.
Figure 11C:
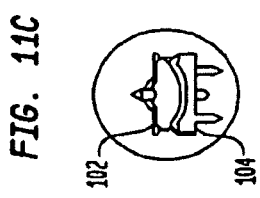
Figure 11A:
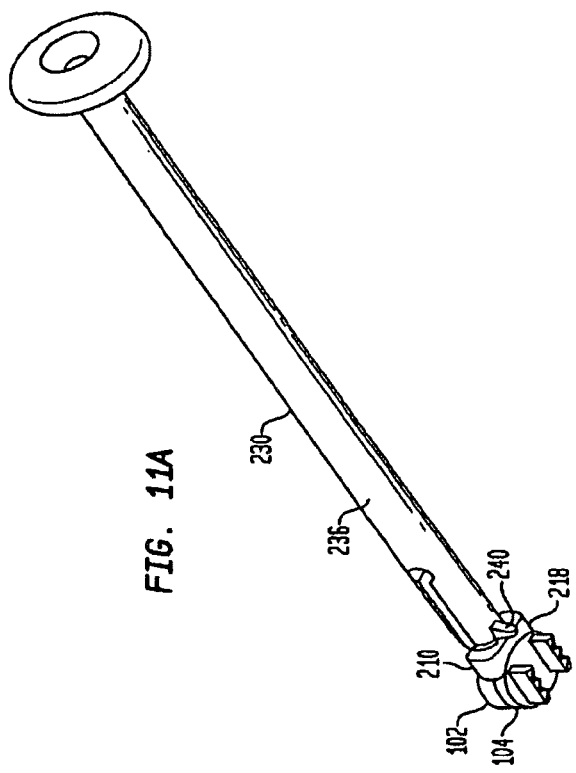

FIGS. 11A-11C show the leading end of the handle 230 of FIGS. 9A-9C secured to the inserter head 210 of FIG. 8A. In turn, the inserter head 210 is holding the top and bottom elements 102, 104 of the intervertebral disc implant. The notches 240 at the leading end of the shaft 236 accommodate the flanges 216, 218 on the inserter head 210.

In certain preferred embodiments of the present invention, the handle 230 is used to insert the implant 100 into a prepared disc space. The correct size of the implant to be inserted into the disc space was preferably previously determined using the combination trial and chisel guide shown and described above in FIGS. 4A-4C. Referring to FIGS. 12A-12C, in order to disengage the implant 100 from the inserter head 210, the shaft 246 of the pusher rod 244 is advanced into the elongated opening extending through the handle 230 and advanced until the leading end of the pusher rod engages the intervertebral disc implant 100. The pusher rod 244 is further advanced for disengaging the implant 100 from the inserter head 210.

Figure 13:
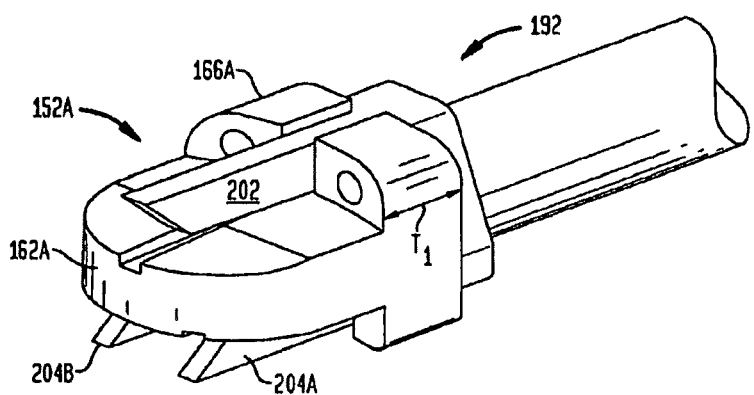
FIG. 13 shows a combination trial and chisel guide, in accordance with one preferred embodiment of the present invention.
Figure 14:
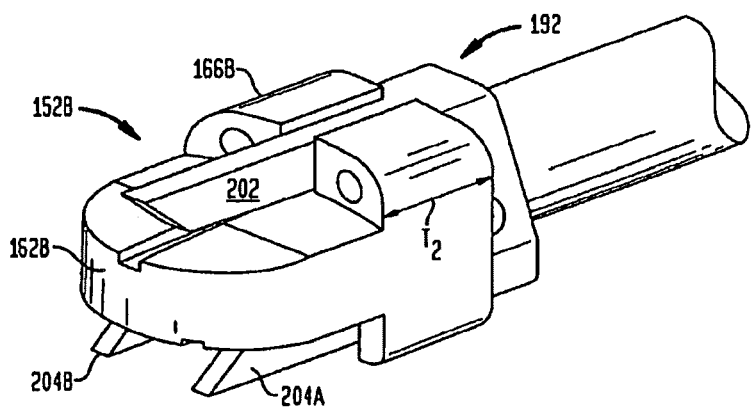
FIG. 14 shows a combination trial and chisel guide, in accordance with another preferred embodiment of the present invention.

Referring to FIGS. 13 and 14, in accordance with certain preferred embodiments of the present invention, a surgical kit includes a plurality of trial and chisel guides 152. The trial and chisel guides 152A, 152B have respective bodies 154A, 154B having the same sizes (i.e. same length, width and height). In the particular embodiment shown in FIGS. 13-14, however, the first trial and chisel guide 152A (FIG. 13) has a flange 166A having a first thickness $T_1$ and the second trial and chisel guide 152B (FIG. 14) has a flange 166B having a second thickness $T_2$. The flange thickness $T_2$ of the second trial and chisel guide 152B is preferably greater than the thickness $T_1$ of the first trial and chisel guide 152A. As shown in FIGS. 13 and 14, the flange thickness controls how far the cutting blades 202, 204A, 204B of the chisel 192 may advance toward the leading ends 162A, 162B of the respective trial and chisel guides 152A, 152B. When the same sized chisel 192 having cutting blades of the same length is used, the different flange thicknesses will control the depth of the channels cut into the vertebral bone. In preferred embodiments, the kit may include a plurality of trial and chisel guides having flanges having different thicknesses. In still other preferred embodiments, a surgical kit may have a plurality of trial and chisel guides having a plurality of different sized bodies and/or a plurality of flanges having different thicknesses and/or a plurality of chisels having cutting blades of different lengths.

Referring to FIGS. 15 and 16, in accordance with certain preferred embodiments of the present invention, a surgical kit includes a plurality of trial and chisel guides 252A and 252B. At least some of the trial and chisel guides 252 in the kit preferably have different sizes. Although only two trial and chisel guides are shown, the kit may include many more trial and chisel guides. In the particular embodiment shown in FIGS. 15-16, a first trial and chisel guide 252A (FIG. 15) has a smaller body 254A and a second trial and chisel guide 252B (FIG. 16) has a larger body 254B. The respective bodies may differ in size by length and/or width and/or thickness. Even though the trial and chisel guides have bodies with different sizes, both guides have flanges 266A, 266B having the same thickness $T_3$. In order to control the depth of the cut into the vertebral bone, chisels having cutting blades having different lengths, widths and/or heights may be provided. In FIG. 15, a first chisel 292A having cutting blades having a length $L_1$ is coupled with trial and chisel guide 252A. In FIG. 16, a second chisel 292B having cutting blades having a length $L_2$ is used. Even though the flange thickness $T_3$ of the respective trial and chisel guides 252A, 252B are the same, the second chisel 292B is able to cut further into bone due to the longer cutting blades 302B, 304A and 304B on the second chisel. In other preferred embodiments, a plurality of chisels having different cutting blade lengths may be used. In still other preferred embodiments, as noted above, a plurality of chisels having cutting blades having different lengths, widths and/or heights may be provided.

Figure 17A:
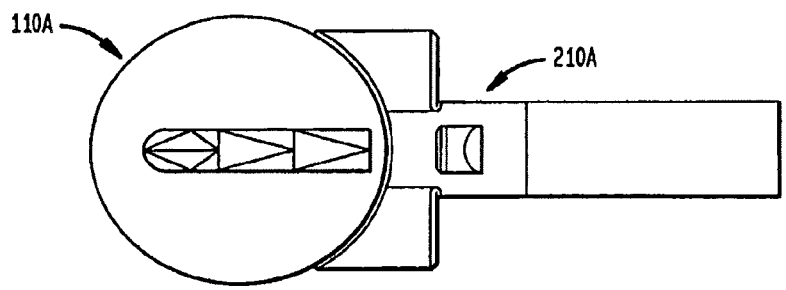
FIGS. 17A-17C show respective top plan, side elevational and cross-sectional views of an intervertebral disc implant coupled with an inserter head, in accordance with certain preferred embodiments of the present invention.
Figure 17B:
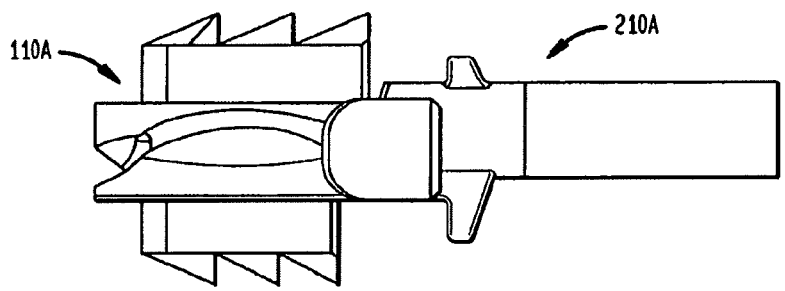
Figure 17C:
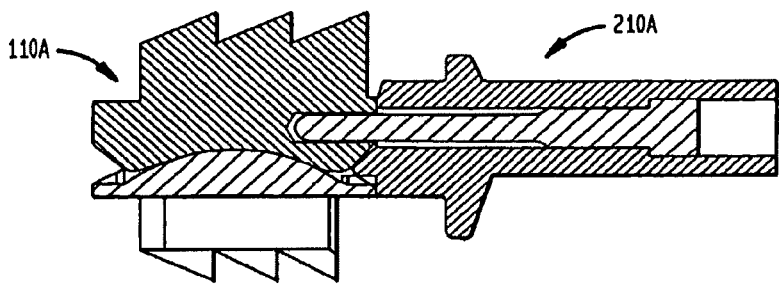
Figure 18A:
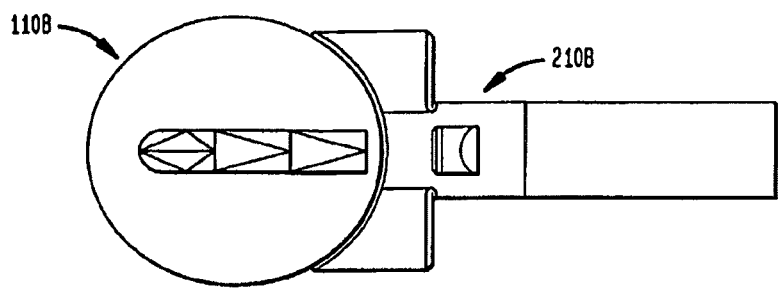
FIGS. 18A-18C show respective top plan, side elevational and cross-sectional views of an intervertebral disc implant coupled with an inserter head, in accordance with further preferred embodiments of the present invention.
Figure 18B:
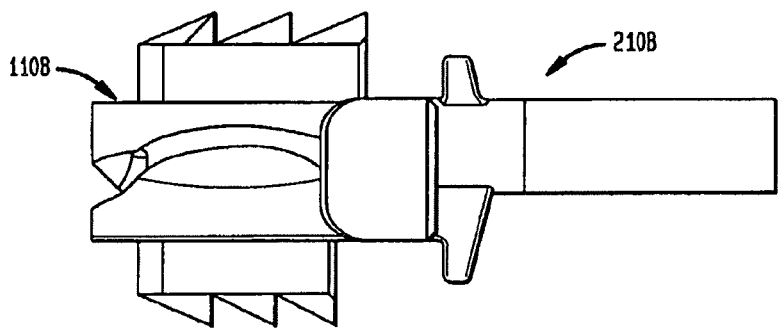
Figure 18C:
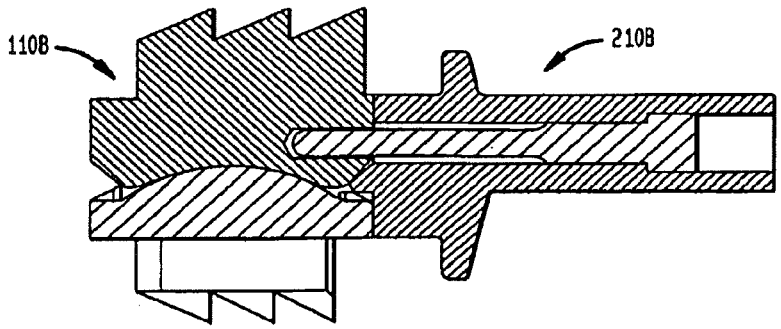

As noted above, in certain preferred embodiments, a plurality of disc implants having different sizes may be provided. The particular size selected for insertion into the disc space is related to the size of the intervertebral space. Each disc implant may be coupled with an inserter head having a size that matches the size of the disc implant. Thus, a plurality of inserter heads having different sizes may be provided, whereby each inserter head is sized to be coupled with an intervertebral disc implant having a particular size. In FIGS. 17A-17C, a first disc implant 110A is coupled with a first inserter head 210A. In FIGS. 18A-18C, a second disc implant 110B, which is larger than the first disc implant 100A, is coupled with a second inserter head 210B that is larger than the first inserter head 210A. Other sized disc implants and inserter heads may also be provided.

In still other preferred embodiments of the present invention, a surgical kit may include chisels having different sizes such as cutting blades having different lengths, widths and/or heights that may be used for forming channels in bone having different lengths, widths and/or heights. The particular chisel selected may relate to the size of the implant being used. In certain preferred embodiments, the differently sized implants have differently sized bone engaging elements (e.g. teeth or bone engaging projections), thereby requiring differently sized trial and chisel guides and/or chisels for preparing the disc spaces.

In certain preferred embodiments, a plurality of inserter heads, each holding a different sized implant, are provided. After the surgeon has determined the correct size needed for the implant, the surgeon will select the appropriate inserter head that holds the correctly sized implant. The surgeon will then attach the inserter head to the leading end of the handle for inserting the implant into the prepared disc space. The handle and the attached inserter head are then removed, leaving the implant in the disc space. The inserter head may then be removed from the handle using the pusher rod.

Prior to implanting the intervertebral disc implant, a review of X-rays, MRI or CT-myelogram is preferably conducted to assess the level to be treated for osteophytes and to compare the intervertebral disc height with the adjacent levels. The patient may be positioned in the supine position to provide for an anterior surgical approach to the cervical spine. Steps should preferably be taken to stabilize the patient's spine in a neutral position and to prevent rotation during the procedure. In certain preferred embodiments, it may be preferable to place a towel or bean bag underneath the patient's shoulders. Tape, a halter or skeletal traction may be used to prevent rotation.

In certain preferred embodiments, a transverse skin incision may be made at the appropriate level to expose the targeted spinal segment including the discs above and below the target spinal segment. Care should be taken to avoid prolonged retraction pressure on vital structures, such as the esophagus.

Another step in the intervertebral disc implantation procedure may involve identifying and marking a midline on the target segment of the spine. In certain preferred embodiments, a template is utilized to mark the midline. The size and dimensions of the template may vary. The exact template size selected may be based upon initial estimation of the appropriate implant size from pre-operative X-rays and/or MRI/CT. In still other preferred embodiments, fluoroscopy may be used to verify the midline and lateral margins of the disc space. In addition, the spinous processes are preferably centered.

A tool such as a scalpel or an electrocautery tool is preferably utilized to score the midline points on the anterior surfaces of the superior and inferior vertebral bodies. Care is preferably taken to ensure that the midline is well defined for all subsequent endplate preparation and implant insertion steps. A cutting tool such as a scalpel may be used to dissect a window in the annulus of the targeted disc. The size of the window dissected in the annulus preferably approximates the width of an intervertebral disc implant to be inserted therein. In certain preferred embodiments, radiographic imaging such as fluoroscopy may be used to identify osteophytes that extend anteriorly. Any osteophytes that extend anteriorly are preferably resected back to the vertebral body so that the surfaces of the superior and inferior vertebral bodies are flattened. Moreover, techniques such as radiographic imaging may be used to identify any osteophytes extending downwardly or upwardly into the anterior region of the disc space. Such osteophytes should be resected to the endplates.

After the targeted spinal segment has been distracted, the discectomy procedure is completed. In preferred embodiments, the posterior and lateral margins of the disc space are cleared of any extraneous matter. The clearing of the lateral and posterior margins preferably extends to the uncinate processes and all the way back to the nerve root and canal. In certain preferred embodiments, lateral fluoroscopy is utilized to check the anterior aspects of the vertebral body for osteophytes. A cutting tool, such as a burr, may be used to further prepare the endplates of the opposing superior and inferior vertebral bodies. The cutting tool may be utilized to smooth out the curvatures of the endplates. After the discectomy has been completed, the endplates of the adjacent vertebral bodies are preferably parallel to one another and relatively uniform, thereby preventing undersizing of the implant.

In certain preferred embodiments, the decompression of the targeted disc space may be completed by removing any posterior osteophytes or soft tissue material that may inhibit the full distraction of the posterior portion of the targeted disc space. In certain preferred embodiments, it may be necessary to remove the posterior longitudinal ligament (PLL) to achieve optimal restoration of the disc height, decompression and release for post-operative motion. In addition, the posteriolateral corners of the endplates may be resected as needed to provide neural decompression. In certain instances, it may be necessary to remove the posteriolateral uncovertebral joints. The lateral uncovertebral joints are preferably not removed unless they are causing nerve root compression. In addition, in certain preferred embodiments it may be necessary to perform a foraminotomy if there are symptoms of neural/foraminal stenosis.

In certain preferred embodiments, an appropriately sized intervertebral disc implant is selected and inserted into a targeted disc space. In certain preferred embodiments, the intervertebral disc implant is provided as a single unit with the top and bottom elements of the implant being held together by an implant dispenser (not shown). In preferred embodiments, the dispenser is color coded to correspond to the height of the implant. In addition, the dispenser is preferably marked with the height of the implant and the width of the top and bottom elements. The outer surface of the implant may also be marked with the height and width of the implant, as well as the inferior/superior orientation. In particular preferred embodiments, the anterior face of the implant is marked with the height and width of the implant.

In preferred embodiments, prior to insertion of the intervertebral disc implant, the size label on the implant is inspected and the size label on the dispenser is also inspected to ensure that the correctly sized implant was selected and that the top element of the implant is oriented for proper insertion. In preferred embodiments, an implant is selected having a height and baseplate dimensions that match the corresponding trial that restored the desired height of the disc space without over-tensioning the annulus or damaging the facets.

After an appropriately sized intervertebral disc implant has been selected, an inserter head, such as the inserter head shown and described above in FIGS. 7A-7C, is selected. The selected inserter head preferably has a height and/or dimensions that match the particular dimensions of the selected implant and selected implant dispenser. Thus, a plurality of insert heads having different sizes may be provided and the inserter heads may also be color coded to correspond to the height of the implant and the particular dimensions of the implant dispenser. The inserter head may be a single use component that is discarded after the implantation procedure.

In certain preferred embodiments, the implant is attached to the inserter head by first matching the superior and inferior labels on the implant dispenser with the inserter head. The pins on the inserter head are then slid into the openings at the anterior ends of the top and bottom elements. The implant is preferably secured to the inserter head when the pins are seated in the openings of the top and bottom elements. Once the implant has been secured to the inserter head, the implant dispenser may be decoupled from the implant. Once secured thereto, the posterior ends of the top and bottom elements of the implant preferably extend beyond the ends of the pins of the inserter head. The implant dispenser may then be detached from engagement with the implant.

In certain preferred embodiments, the intervertebral disc implant is inserted into a prepared disc space. The inserter head is properly oriented with the disc space. In preferred embodiments, the inserter head includes at least one label or marking that is oriented relative to the superior or inferior vertebral bodies. Preferably, a superior label of the inserter head is oriented on top and an inferior label is oriented on the bottom. As the intervertebral disc is advanced toward the disc space, the implant protrusions/teeth are preferably aligned with the openings previously formed in the endplates. In certain preferred embodiments, fluoroscopy is utilized to check the angle of insertion of the implant. In certain preferred embodiments, the inserter head is preferably advanced toward the disc space until the upper and lower flanges of the inserter head come into contact with the anterior surfaces of the adjacent vertebral bodies.

In certain preferred embodiments, insertion is completed when the implant is fully disengaged from the inserter head and the top and bottom elements of the implant are positioned between the superior and inferior vertebral bodies. The anterior/posterior positioning of the implant is preferably confirmed to be satisfactory using fluoroscopy. If more posterior positioning of either the top element or the bottom element of the intervertebral disc implant is required, a tamp may be utilized for adjusting the position of the implant. In preferred embodiments, the tamp may be impacted to adjust the anterior/posterior depth of the top and bottom elements of the implant.

An intraoperative lateral and anterior/posterior image of the implant may be obtained to observe its final position. If the implant is not properly positioned, it may be removed such as by using an extractor. Once it has been confirmed that the intervertebral disc is properly positioned within the disc space, a standard surgical closure procedure for anterior spinal surgery may be performed. Prior to discharge from the hospital, a lateral and anterior/posterior X-ray with the patient in the standing and/or sitting position is preferred.

Following surgery, in certain preferred embodiments, a goal of post-operative rehabilitation is to return the patient to normal activity as soon as possible without jeopardizing soft and hard tissue healing. Preferably, the patient should wear a soft collar for approximately 1-2 weeks to support healing of the incision. The patient's rehabilitation program may be modified under the direction of a surgeon to take into consideration the patient's age, stage of healing, general health, physical condition, life-style, and activity goals. Adherence to a recommended rehabilitation program is highly desirable.

Disclosed herein are implants, surgical instruments and procedures in accordance with certain preferred embodiments of the present invention. It is contemplated, however, that the implants, instruments and procedures may be slightly modified, and/or used in whole or in part and with or without other instruments and procedures, and still fall within the scope of the present invention. Although the present invention may discuss a series of steps in a procedure, the steps may be accomplished in a different order, or may be used individually, or in conjunction with other methods, without deviating from the scope of the present invention.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

INDUSTRIAL APPLICABILITY

The present invention enjoys wide industrial applicability including, but not limited to, providing implants and instruments useful in spinal surgery.

The invention claimed is:
1. An artificial intervertebral disc kit for the spine comprising:
a plurality of artificial intervertebral discs of different sizes, each artificial intervertebral disc having first and second elements sized for insertion into a disc space between first and second adjacent vertebral bodies, the first and second elements being moveable with the first and second vertebral bodies during flexion, extension, and lateral bending of the first and second vertebral bodies;
a plurality of inserter heads each being detachably engaged in a pre-attached manner with a corresponding one of the artificial intervertebral discs such that each inserter head simultaneously holds the first and second elements of their corresponding artificial intervertebral disc so that the plurality of inserter heads and their corresponding artificial intervertebral disc are each a part of a single unit for insertion into the disc space; and
an inserter handle detachably engageable with each inserter head holding its corresponding artificial intervertebral disc such that the inserter head and its corresponding artificial intervertebral disc are manipulatable, via the inserter handle, as a unit for insertion of the corresponding artificial intervertebral disc into the disc space,
wherein each of the plurality of inserter heads is configured to pre-attach with its corresponding artificial intervertebral disc such that each of the plurality of inserter heads simultaneously holds the first and second elements of its corresponding artificial intervertebral disc in a fixed relationship before any one of the plurality of inserter heads is engaged by the inserter handle.

2. The artificial intervertebral disc kit as claimed in claim 1, wherein at least one of the first and second elements of each artificial intervertebral disc has an opening, and each inserter head has a protrusion engageable with the opening of its corresponding artificial intervertebral disc.

3. The artificial intervertebral disc kit as claimed in claim 2, wherein the opening is positioned on a perimeter surface of the at least one of the first and second elements of each artificial intervertebral disc.

4. The artificial intervertebral disc kit as claimed in claim 1, wherein the second element of each artificial intervertebral disc has first and second openings and each inserter head has first and second protrusions engageable with the first and second openings of its corresponding artificial intervertebral disc, respectively.

5. The artificial intervertebral disc kit as claimed in claim 1, wherein each inserter head includes a stem extending outwards from a body of the inserter head, and the inserter handle includes a bore sized to receive each stem for engagement of the inserter handle with a selected one of the inserter heads.

6. The artificial intervertebral disc kit as claimed in claim 1, wherein the inserter handle is detachably engageable with each insert head via a male-female connection.

7. The artificial intervertebral disc kit as claimed in claim 1, wherein the first and second elements of each of the artificial intervertebral discs have corresponding articular surfaces that articulate with each other during flexion, extension, and lateral bending of the first and second vertebral bodies and when implanted.

8. The artificial intervertebral disc kit as claimed in claim 7, wherein, when the inserter heads are each pre-attached with the corresponding artificial intervertebral disc, the articular surfaces of the first and second elements of the corresponding artificial intervertebral disc are held in registration with each other via the inserter head.

9. The artificial intervertebral disc kit as claimed in claim 7, wherein the first and second elements of each of the artificial intervertebral discs include a bone contact surface opposite the articular surface.

10. The artificial intervertebral disc kit as claimed in claim 7, wherein at least one of the articular surfaces of the first and second elements of each of the artificial intervertebral discs define a concave surface.

11. The artificial intervertebral disc kit as claimed in claim 1, wherein each of the plurality of inserter heads includes a proximal end and a distal end, the proximal end of each of the inserter heads being configured to detachably engage a distal end of the inserter handle so that the inserter head extends only along a partial length of the inserter handle when engaged thereto so that a proximal end of the inserter handle defines a proximal extent of an inserter instrument comprised of both the inserter handle and a selected one of the plurality of inserter heads for engagement.

12. An artificial intervertebral disc kit for the spine comprising:
an artificial intervertebral disc having first and second elements sized for insertion into a disc space between first and second adjacent vertebral bodies, the first and second elements being moveable with the first and second vertebral bodies during flexion, extension, and lateral bending of the first and second vertebral bodies;
an inserter head having a leading end and a trailing end, the leading end being detachably engageable with the artificial intervertebral disc such that the inserter head simultaneously holds the first and second elements of the artificial intervertebral disc so that the inserter head and artificial intervertebral disc are each a part of a single unit for insertion into the disc space; and
an inserter handle having a leading end and a trailing end remote from the leading end, the leading end being detachably engageable with the trailing end of the inserter head, such that the inserter head and artificial intervertebral disc are manipulatable, via the inserter handle, as a unit for insertion of the artificial intervertebral disc into the disc space,
wherein the inserter head is configured to detachably engage the first and second elements of the artificial intervertebral disc in a pre-attached manner such that the first and second elements are simultaneously held in a fixed relationship by the inserter head prior to the inserter head being engaged by the inserter handle.

13. The artificial intervertebral disc kit as claimed in claim 12, wherein at least one of the first and second elements has an opening, and the inserter head has a protrusion engageable with the opening.

14. The artificial intervertebral disc kit as claimed in claim 13, wherein the protrusion is a resilient pin for urging the at least one of the first and second elements into securement with the inserter head.

15. The artificial intervertebral disc kit as claimed in claim 13, wherein the second element has first and second openings and the inserter head has first and second protrusions engageable with the first and second openings, respectively.

16. The artificial intervertebral disc kit as claimed in claim 15, wherein a projection extends upwards from the inserter head and is effective to limit an insertion depth of the artificial intervertebral disc into the disc space.

17. The artificial intervertebral disc kit as claimed in claim 12, wherein the trailing end of the inserter head is configured to detachably engage the leading end of the inserter handle such that the inserter head extends only along a partial length of the inserter handle so that the trailing end of the inserter handle defines a trailing end extent of an inserter instrument comprised of both the inserter head and inserter handle.

18. The artificial intervertebral disc kit as claimed in claim 12, wherein the first and second elements each include an articular surface and a bone contact surface disposed opposite the articular surface.

19. The artificial intervertebral disc kit as claimed in claim 18, wherein, when the inserter head is each pre-attached with the artificial intervertebral disc, the articular surfaces of the first and second elements are held in registration with each other via the inserter head.

20. The artificial intervertebral disc kit as claimed in claim 18, wherein at least one of the articular surfaces of the first and second elements of each of the artificial intervertebral discs define a concave surface.

* * * * *